(12) United States Patent
Jachmann et al.

(10) Patent No.: US 9,784,881 B2
(45) Date of Patent: Oct. 10, 2017

(54) NUCLEAR MAGNETIC RESONANCE APPARATUS, SYSTEMS, AND METHODS

(71) Applicant: Halliburton Energy Services, Inc., Houston, TX (US)

(72) Inventors: Rebecca Corina Jachmann, Spring, TX (US); Lilong Li, Humble, TX (US); Arcady Reiderman, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/103,782

(22) PCT Filed: Feb. 10, 2016

(86) PCT No.: PCT/US2016/017309
§ 371 (c)(1),
(2) Date: Jun. 10, 2016

(87) PCT Pub. No.: WO2016/140783
PCT Pub. Date: Sep. 9, 2016

(65) Prior Publication Data
US 2017/0003413 A1 Jan. 5, 2017

Related U.S. Application Data

(60) Provisional application No. 62/128,746, filed on Mar. 5, 2015.

(51) Int. Cl.
*G01V 3/32* (2006.01)
*E21B 47/00* (2012.01)
(Continued)

(52) U.S. Cl.
CPC ............... *G01V 3/32* (2013.01); *E21B 47/00* (2013.01); *G01N 24/081* (2013.01);
(Continued)

(58) Field of Classification Search
CPC ... G01V 3/32; G01V 3/30; G01V 3/18; G01V 3/20; G01V 3/26; G01R 33/44;
(Continued)

(56) References Cited

U.S. PATENT DOCUMENTS 5,196,748 A 3/1993 Rigney
5,432,446 A * 7/1995 MacInnis ................. G01V 3/32
324/303

(Continued)

OTHER PUBLICATIONS

"International Application Serial No. PCT/US2016/017309, International Search Report mailed May 12, 2016", 3 pgs.

(Continued)

*Primary Examiner* — Melissa Koval
*Assistant Examiner* — Rishi Patel
(74) *Attorney, Agent, or Firm* — Gilliam IP PLLC

(57) ABSTRACT

Apparatus and systems include a magnet assembly comprising a central magnet having a first axial end and a second, opposite axial end; a first end piece magnet having a proximal end and a distal end, the proximal end spaced apart from the first axial end of the central magnet; and a second end piece magnet spaced apart from the second axial end of the central magnet; at least one first shim magnet disposed adjacent to or at least partially surrounded by first magnetically permeable material, the at least one first shim magnet disposed next to an end of the first end piece magnet that is proximal to the central magnet, or next to an end of the first end piece magnet that is distal to the central magnet; and a downhole tool attached to the magnet assembly. Additional apparatus, systems, and methods are disclosed.

19 Claims, 22 Drawing Sheets

(51) Int. Cl.
*G01R 33/34* (2006.01)
*G01R 33/44* (2006.01)
*G01R 33/3875* (2006.01)
*G01V 3/18* (2006.01)
*G01N 24/08* (2006.01)
*G01R 33/38* (2006.01)
*G01R 33/3873* (2006.01)
*G01R 33/36* (2006.01)

(52) U.S. Cl.
CPC ... *G01R 33/34092* (2013.01); *G01R 33/3808* (2013.01); *G01R 33/3873* (2013.01); *G01R 33/3875* (2013.01); *G01R 33/44* (2013.01); *G01V 3/18* (2013.01); *G01R 33/3678* (2013.01)

(58) Field of Classification Search
CPC .......... G01R 33/34092; G01R 33/3875; G01R 33/383; G01R 33/3803; G01R 33/445; G01R 33/3678; G01R 33/3808; G01R 33/3873; E21B 47/00; G01N 24/081
USPC ........................................... 324/303
See application file for complete search history.

(56) References Cited

U.S. PATENT DOCUMENTS

| | | | |
|---|---|---|---|
| 5,705,927 A * | 1/1998 | Sezginer | G01N 24/081 324/303 |
| 5,828,214 A | 10/1998 | Taicher et al. | |
| 6,215,304 B1 * | 4/2001 | Slade | G01N 24/081 324/303 |
| 2002/0196018 A1 | 12/2002 | Wisler et al. | |
| 2004/0066194 A1 * | 4/2004 | Slade | G01R 33/3808 324/318 |
| 2004/0119471 A1 * | 6/2004 | Blanz | E21B 49/00 324/303 |
| 2009/0072825 A1 | 3/2009 | Prammer et al. | |
| 2011/0006775 A1 | 1/2011 | Fang et al. | |

OTHER PUBLICATIONS

"International Application Serial No. PCT/US2016/017309, Written Opinion mailed May 12, 2016", 4 pgs.

* cited by examiner

US 9,784,881 B2

NUCLEAR MAGNETIC RESONANCE APPARATUS, SYSTEMS, AND METHODS

This application is a U.S. National Stage Filing under 35 U.S.C. §371 from International Application No. PCT/US2016/017309, filed on Feb. 10, 2016, which application claims the benefit of priority to U.S. Provisional Application Ser. No. 62/128,746, filed on Mar. 5, 2015which applications are hereby incorporated herein by reference in their entirety.

CLAIM FOR PRIORITY

This application claims priority to U.S. Provisional Application Ser. No. 62/128,746, filed on Mar. 5, 2015 which application is hereby incorporated herein by reference in its entirety.

BACKGROUND

In the field of logging (e.g. wireline logging, logging while drilling (LWD) and measurement while drilling (MWD)), nuclear magnetic resonance (NMR) tools have been used to explore geographic formations based on the magnetic interactions with subsurface material. Some downhole NMR tools include a magnet assembly that produces a static magnetic field, and a coil assembly that generates radio frequency (RF) control signals and detects magnetic resonance phenomena in the subsurface material. Properties of the subsurface material can be identified from the detected phenomena.

When using NMR-based tools, it can be difficult to achieve a satisfactory signal-to-noise ratio (SNR) based on the natural polarization of the spins. In addition, the ex situ (i.e., outward looking) nature of downhole NMR tools means that the excitation field naturally falls off in strength over distance from the tool. Thus, the further the antenna is from the sensitive volume, the lower the amplitude of the corresponding received signal.

DETAILED DESCRIPTION

In some embodiments, an NMR-based tool can be constructed to provide subsurface data with an improved SNR. For example, a tool constructed according to various embodiments disclosed herein may include strategically placed magnets, magnetically permeable material, and copper to provide a higher SNR at a given distance into the formation than conventional tools can offer.

Some examples include a magnet assembly to produce a magnetic field in a volume in a geological formation, the magnet assembly comprising a central magnet having a first axial end and a second, opposite axial end; a first end piece magnet spaced apart from the first axial end of the central magnet; and a second end piece magnet spaced apart from the second axial end of the central magnet. The magnet assembly also comprises at least one shim magnet disposed between the central magnet and the first end piece magnet, the shim magnet disposed adjacent to or at least partially surrounded by a magnetically permeable material, the shim magnet to shape a static magnetic field sub-volume provided by the central magnet and the first end piece magnet. A downhole tool may be attached to the magnet assembly. These and many other embodiments will now be described in detail.

Figure 1A:
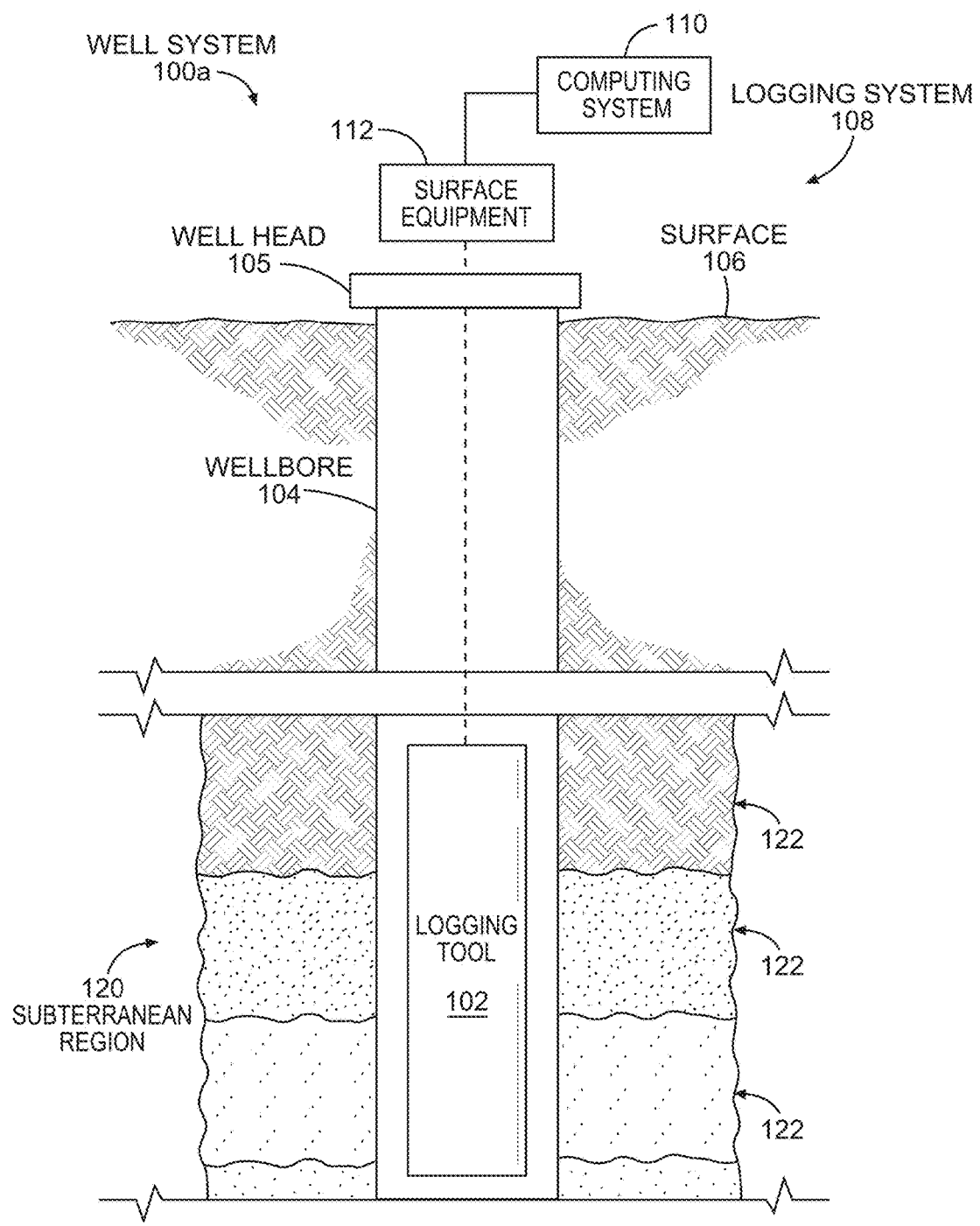
FIG. 1A is a diagram of an example well system, according to various embodiments.

FIG. 1A is a diagram of an example well system 100a, according to various embodiments. The example well system 100a includes an NMR logging system 108 and a subterranean region 120 beneath the ground surface 106. A well system can include additional or different features that are not shown in FIG. 1A. For example, the well system 100a may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slanted wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 10 can be implemented as a component of, or can be integrated with one or more components of, the surface equipment 112, the logging tool 102 or both. In some cases, the computing subsystem 110 can be implemented as one or more computing structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allows communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for optical telemetry, wireline telemetry, wired pipe telemetry, mud pulse telemetry, acoustic telemetry, electromagnetic telemetry, or a combination of these and other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 2A:
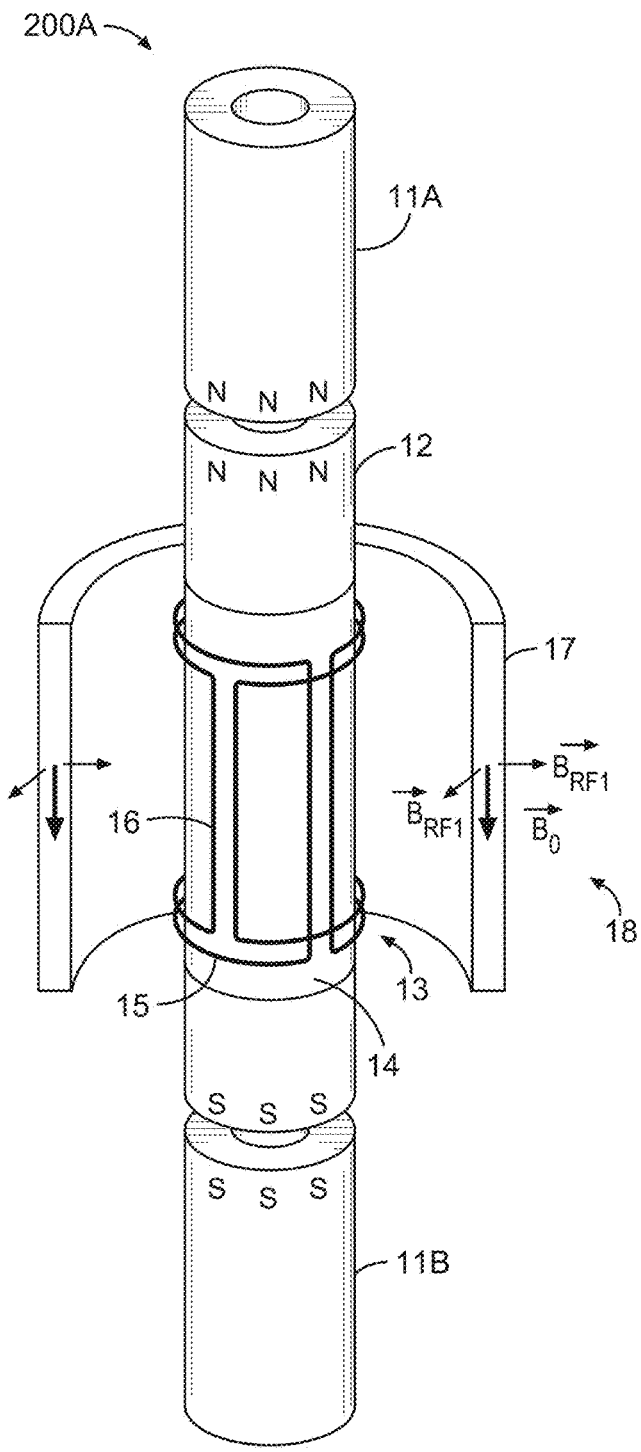
FIG. 2A is a diagram of an example downhole tool for obtaining NMR data from a subterranean region, according to various embodiments.
Figure 2B:
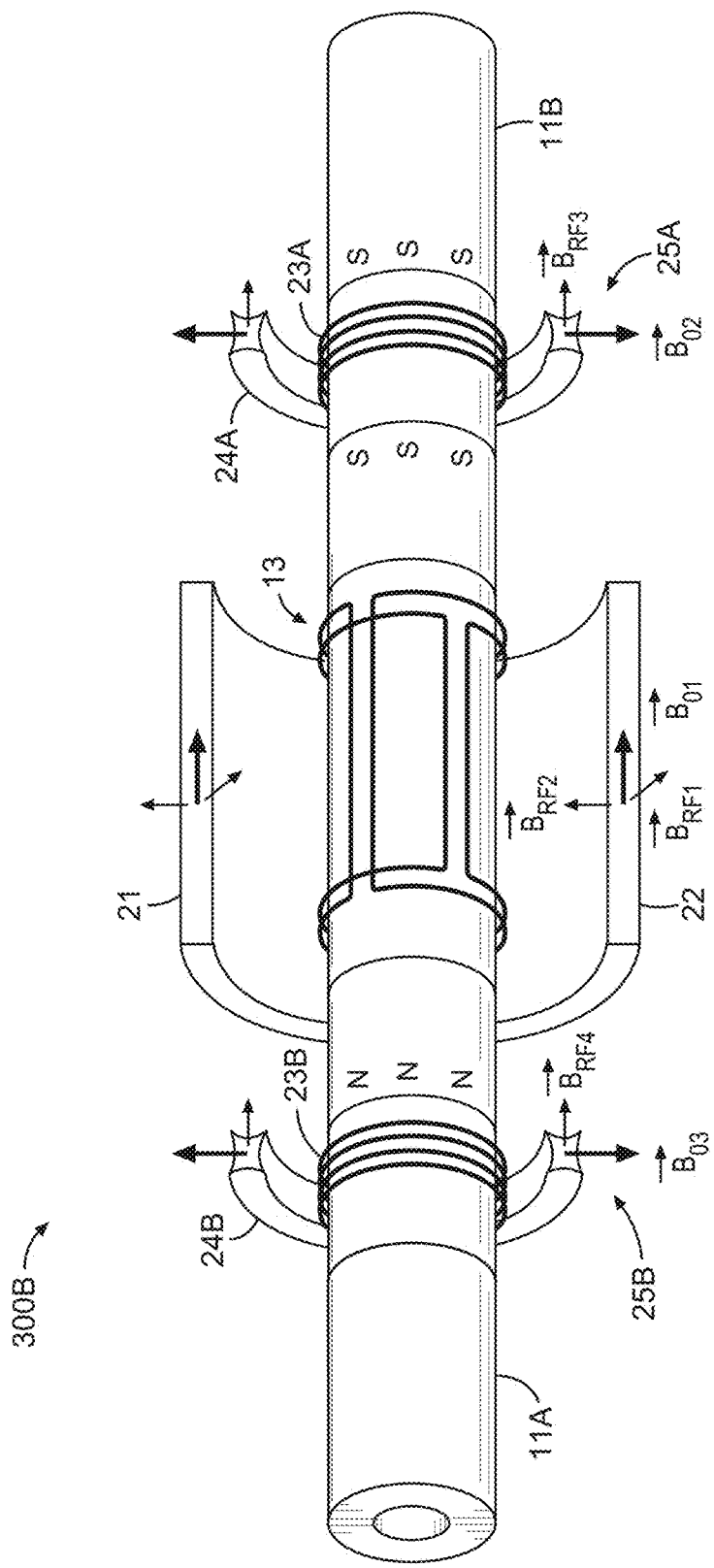
FIG. 2B is a diagram of another example downhole tool for obtaining NMR data from a subterranean region, according to various embodiments.

In some implementations, the logging tool 102 includes a magnet assembly that includes a central magnet and two end piece magnets. Examples are shown in FIGS. 2A, 2B, and 3B. The end piece magnets can be spaced apart from the axial ends of the central magnet. The end pieces together with the central magnets can define four magnetic poles, which may be arranged to enhance the static magnetic field in a volume of interest. In some cases, the central magnet defines a first magnetic field orientation, and the end piece magnets define a second magnetic field orientation that is orthogonal to the first magnetic field orientation. The logging tool 102 can also include multiple orthogonal transversal-dipole antennas. The orthogonal transversal-dipole antennas can produce circular polarized excitation in a subterranean volume and acquire a response from the volume by quadrature coil detection.

In some implementations, the logging tool 102 includes a magnet assembly that produces a magnetic field in multiple distinct sub-volumes in the subterranean region 120. An example is shown in FIG. 2B. A first sub-volume can be an elongate cylindrical-shell region that extends in the longitudinal direction (parallel to the wellbore axis), and the magnetic field in the first sub-volume can be substantially uniformly oriented along the longitudinal direction. Second and third sub-volumes can be spaced apart from the axial ends of the first sub-volume, and the static magnetic field in the second and third sub-volumes can have a radial orientation (perpendicular to the longitudinal direction). The second and third sub-volumes can be located at a different distance from the center of the tool string than the first volume. In some instances, the locations of the second and third sub-volumes allow the logging tool to collect information for mud filtrate invasion profiling. The logging tool 102 can also include multiple antenna assemblies at respective locations along the longitudinal axis. Each of the antenna assemblies can detect an NMR response from a respective one of the distinct sub-volumes.

In some implementations, the logging tool 102 includes a magnet assembly and a transversal-dipole and monopole antenna assembly. An example is shown in FIG. 3B. The transversal-dipole and monopole antenna assembly can obtain a unidirectional azimuthally-selective NMR response from a subterranean volume about the magnet assembly. The transversal-dipole and monopole antenna assembly can include orthogonal transversal-dipole antennas and a monopole antenna.

Figure 1B:
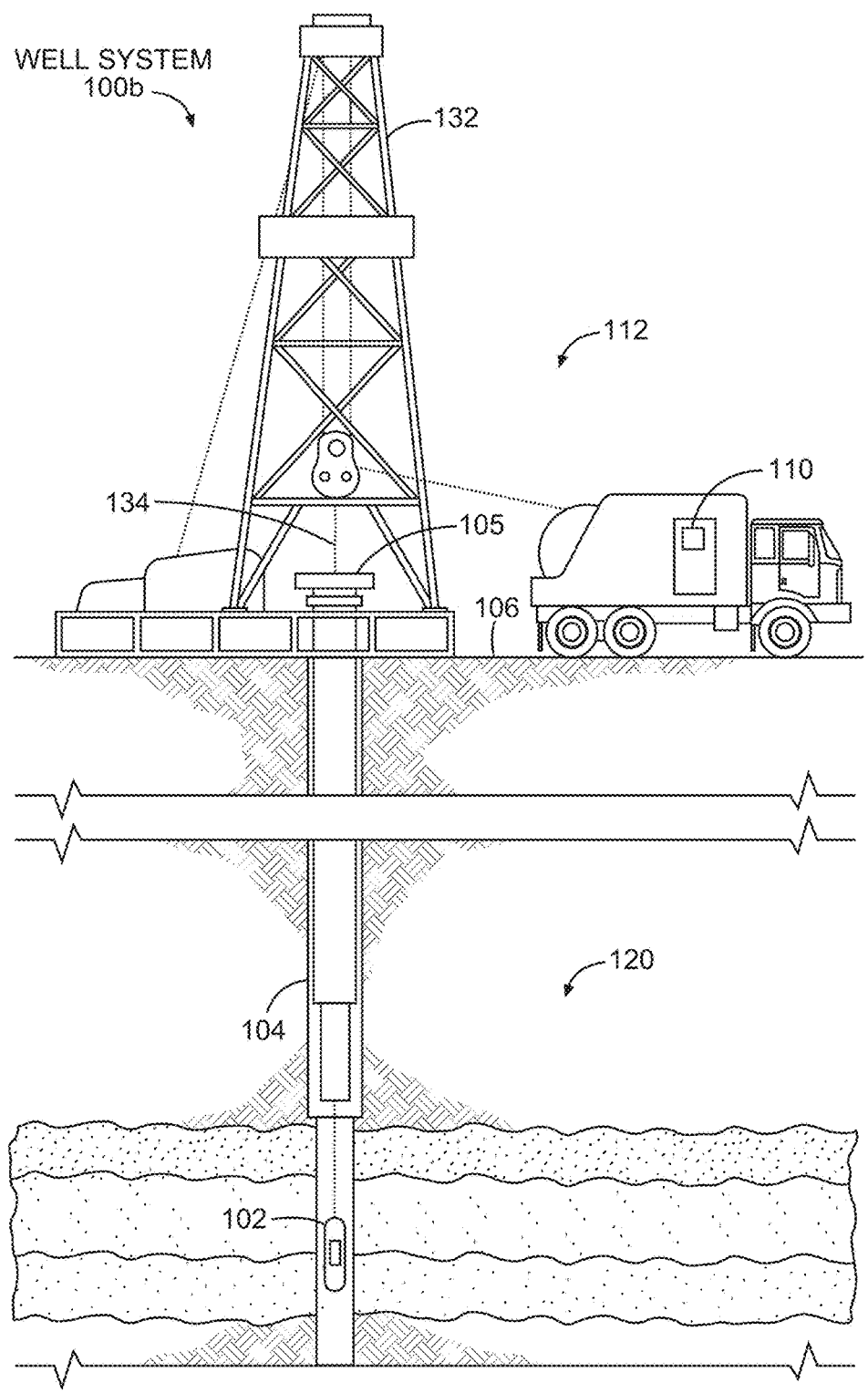
FIG. 1B is a diagram of an example well system that includes an NMR tool in a wireline logging environment, according to various embodiments.

In some examples, NMR logging operations are performed during wireline logging operations. FIG. 1B is a diagram of an example well system 100b that includes an NMR tool in a wireline logging environment, according to various embodiments. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
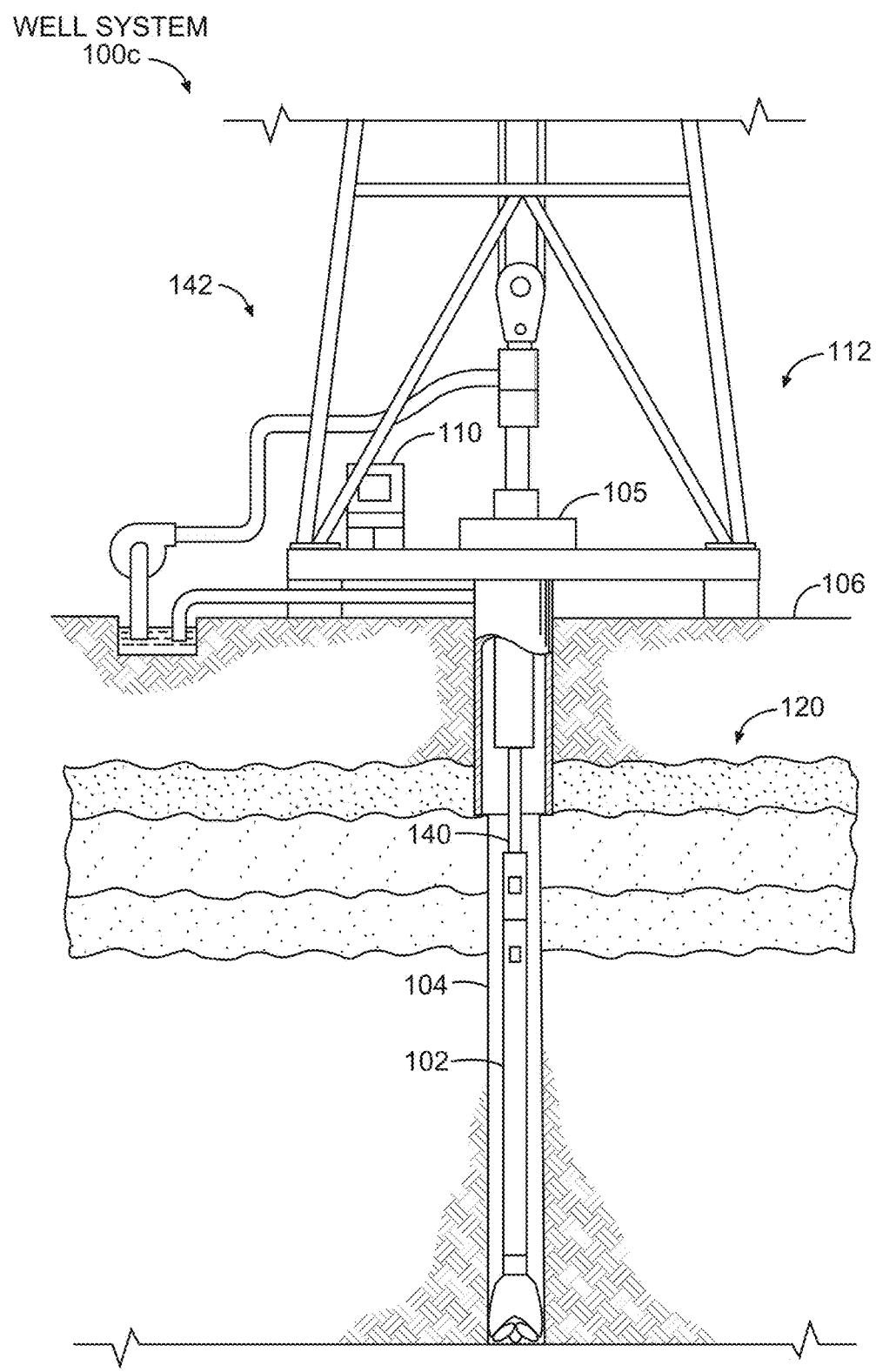
FIG. 1C is a diagram of an example well system that includes an NMR tool in a logging while drilling (LWD) environment, according to various embodiments.

In some examples, NMR logging operations are performed during drilling operations. FIG. 1C is a diagram of an example well system 100c that includes an NMR tool in a logging while drilling (LWD) environment, according to various embodiments. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a Kelly, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

In some implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, viscosity, porosity, material content, or other properties of the subsurface layers 122 based on the NMR measurements acquired by the logging tool 102 in the wellbore 104.

In some implementations, the logging tool 102 obtains NMR signals by polarizing nuclear spins in the subterranean region 120 and pulsing the nuclei with a radio frequency (RF) magnetic field. Various pulse sequences (i.e., series of radio frequency pulses, delays, and other operations) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

The acquired spin-echo signals (or other NMR data) may be processed (e.g., inverted, transformed, etc.) to a relaxation-time distribution (e.g., a distribution of transverse relaxation times $T_2$ or a distribution of longitudinal relaxation times $T_1$), or both. A diffusion axis D is also possible. The relaxation-time distribution can be used to determine various physical properties of the formation by solving one or more inverse problems. In some cases, relaxation-time distributions are acquired for multiple logging points and used to train a model of the subterranean region. In some cases, relaxation-time distributions are acquired for multiple logging points and used to predict properties of the subterranean region.

FIG. 2A is a diagram of an example downhole tool 200A for obtaining NMR data from a subterranean region, according to various embodiments. The example NMR tool 200A includes a magnet assembly that generates a static magnetic field to produce polarization, and an antenna assembly that (a) generates a radio frequency (RF) magnetic field to generate excitation, and (b) acquires NMR signals. In the example shown in FIG. 2A, the magnet assembly that includes the end piece magnets 11A, 11B and a central magnet 12 generates the static magnetic field in the volume of investigation 17. In the volume of investigation 17, the direction of the static magnetic field (shown as the solid black arrow 18) is parallel to the longitudinal axis of the wellbore. In some examples, a magnet configuration with double pole strength can be used to increase the strength of the magnetic field (e.g., up to 100-150 Gauss or higher in some instances).

In the example shown in FIG. 2A, the antenna assembly 13 includes two mutually orthogonal transversal-dipole antennas 15, 16. In some instances, the NMR tool 200A can be implemented with a single transversal-dipole antenna. For example, one of the transversal-dipole antennas 15, 16 may be omitted from the antenna assembly 13. The example transversal-dipole antennas 15, 16 shown in FIG. 2A are placed on an outer surface of a soft magnetic core 14, which is used for RF magnetic flux concentration. The static magnetic field can be axially symmetric (or substantially axially symmetric), and therefore may not require broader band excitation associated with additional energy loss. The volume of investigation can be made axially long enough and thick enough (e.g., 20 cm long, and 0.5 cm thick in some environments) to provide immunity or otherwise decrease sensitivity to axial motion, lateral motion, or both. A longer sensitivity region can enable measurement while tripping the drill string. The sensitivity region can be shaped by shaping the magnets 11A, 11B, 12 and the soft magnetic material of the core 14.

In some implementations, the antenna assembly 13 additionally or alternatively includes an integrated coil set that performs the operations of the two transversal-dipole antennas 15, 16. For example, the integrated coil may be used (e.g., instead of the two transversal-dipole antennas 15, 16) to produce circular polarization and perform quadrature coil detection. Examples of integrated coil sets that can be adapted to perform such operations include multi-coil or complex single-coil arrangements, such as, for example, birdcage coils commonly used for high-field magnetic resonance imaging (MRI).

Compared to some example axially-symmetrical designs, the use of the longitudinal-dipole magnet and the transversal-dipole antenna assembly also has an advantage of less eddy current losses in the formation and drilling fluid (i.e., "mud") in the wellbore due to a longer eddy current path than for some longitudinal-dipole antenna(s).

In some aspects, NMR measurements over multiple sub-volumes can increase the data density and therefore SNR per unit time. Multiple volume measurements in a static magnetic field having a radial gradient can be achieved, for example, by acquiring NMR data on a second frequency while waiting for nuclear magnetization to recover (e.g., after a CPMG pulse train) on a first frequency. A number of different frequencies can be used to run a multi-frequency NMR acquisition involving a number of excitation volumes with a different depth of investigation (DOI). In addition to higher SNR, the multi-frequency measurements can also enable profiling the fluid invasion in the wellbore, enabling a better assessment of permeability of earth formations. Another way to conduct multi-volume measurements is to use different regions of the magnet assembly to acquire an NMR signal. NMR measurements of these different regions can be run at the same time (e.g., simultaneously) or at different times.

FIG. 2B is a diagram of another example downhole tool 200B for obtaining NMR data from a subterranean region, according to various embodiments. The example NMR tool 200B also includes a magnet assembly that generates a static magnetic field to produce polarization, and an antenna assembly that (a) generates a radio frequency (RF) magnetic field to generate excitation, and (b) acquires NMR signals. In the example shown in FIG. 2B, the magnet assembly produces a magnetic field having a dominant axial component in the volume of investigation 21. The directions of the RF magnetic field (produced by two transversal dipole antennas as in FIG. 2A) and the static magnetic field in this region are shown at 22. In the example shown in FIG. 2B, two distinct volumes of investigation 24A, 24B are created near the magnet poles (beyond the axial ends of the central magnet) where the static magnetic field has a predominantly radial component. The example NMR antennas shown at 23A and 23B can generate RF magnetic fields in the volumes of investigation 24A and 24B near the longitudinal-dipole antennas. The longitudinal direction of the RF magnetic fields in the volumes of investigation 24A and 24B, and the radial direction of the static magnetic field in the volumes of investigation 24A and 24B, are shown at 25A and 25B.

In some aspects, a combination of transversal-dipole and monopole antennas can be used to enable unidirectional azimuthally-selective measurements, without substantially reducing SNR in some cases. In some examples, the NMR excitation can be substantially axially symmetrical (e.g., using either the transversal-dipole antenna or the monopole antenna) while a combination of axially-symmetrical sensitivity transversal-dipole antenna and the axially-symmetrical sensitivity monopole antenna responses can enable azimuthally-resolved measurements.

Figure 3A:
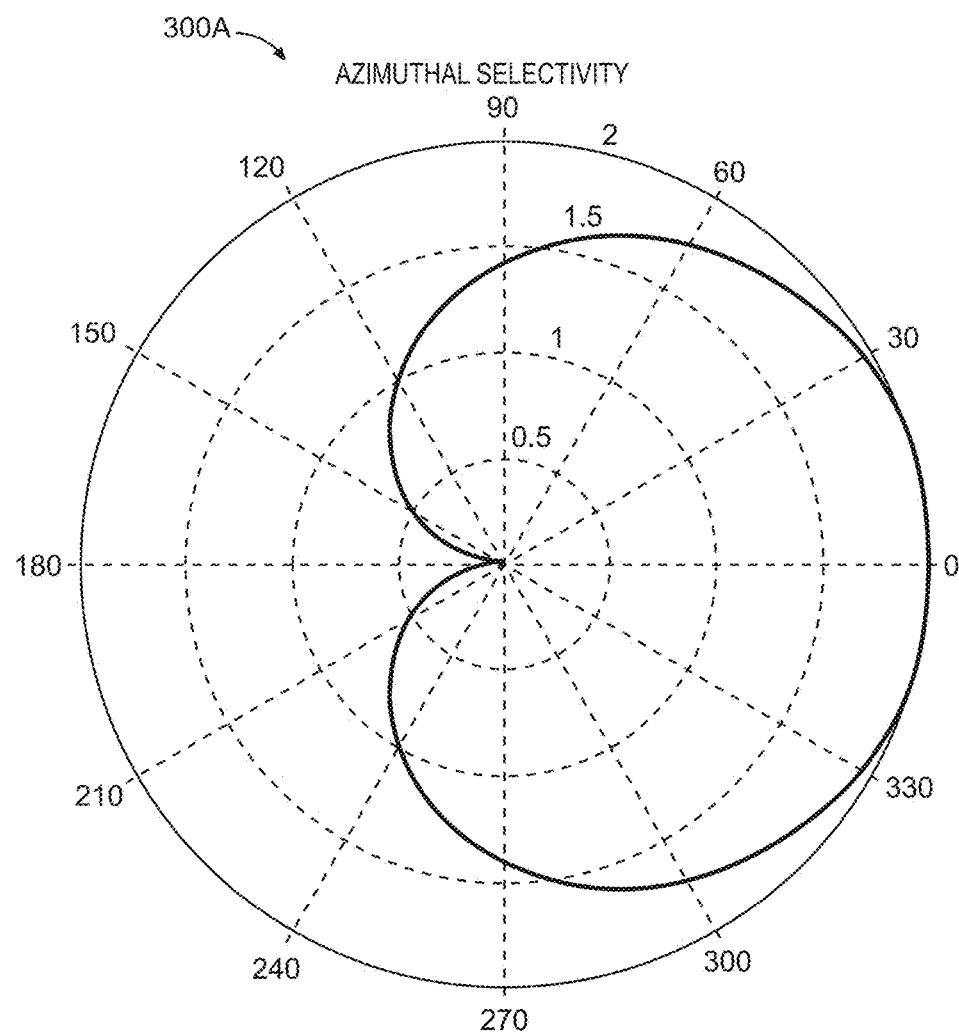
FIG. 3A is a plot showing azimuthal selectivity for an example downhole tool, according to various embodiments.
Figure 3B:
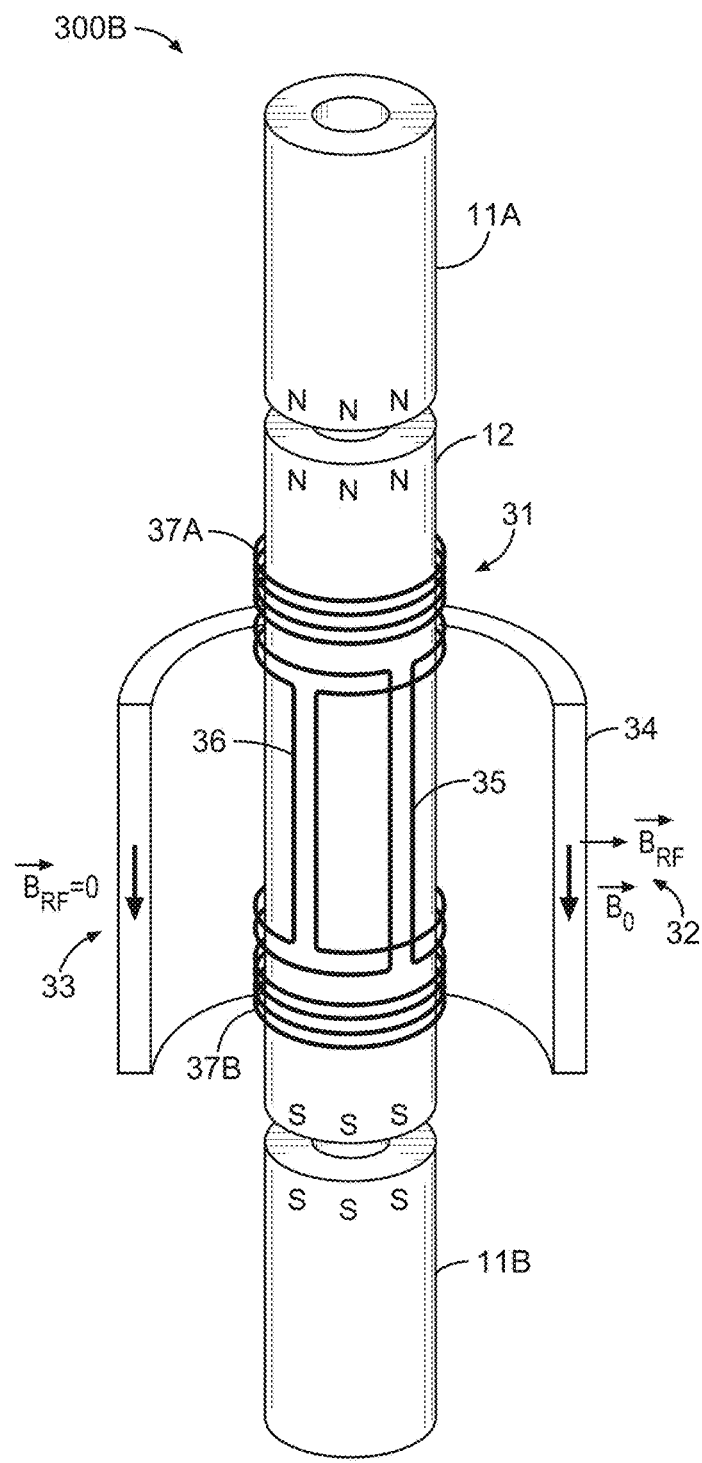
FIG. 3B is a diagram of another example downhole tool for obtaining NMR data from a subterranean region, according to various embodiments.

FIGS. 3A and 3B illustrate aspects of an example azimuthally-selective NMR tool. FIG. 3A is a plot 300A showing azimuthal selectivity for an example downhole tool 300B, according to various embodiments. The example NMR tool 300B includes a magnet assembly that generates a static magnetic field to produce polarization, and an antenna assembly that (a) generates a radio frequency (RF) magnetic field to generate excitation, and (b) acquires NMR signals. The antenna assembly 31 shown in FIG. 3B includes a substantially monopole antenna and two orthogonal transversal-dipole antennas 35 and 36. The example monopole antenna includes two coils 37A and 37B connected in reverse polarity in order to generate a substantially radial RF magnetic field in the volume of investigation 34. Due to reciprocity, the same coil arrangement can have a radial sensitivity direction. The example RF magnetic fields BRF presented at 32 and 33 can reflect the total sensitivity direction when the monopole antenna response is combined with one of the transversal-dipole antenna responses.

FIG. 3B is a diagram of another example downhole tool for obtaining NMR data from a subterranean region, according to various embodiments. The example monopole antenna shown in FIG. 3B includes an arrangement of coils that generate locally a substantially radially-directed magnetic field, i.e., the field that would be produced by a single "magnetic charge" or magnetic pole. Here, the term "monopole" is used to distinguish this type of magnetic field from a dipole magnetic field (transversal or longitudinal). In some cases, the monopole antenna assembly generates quasi-stationary (relatively low frequency) magnetic fields. In the example shown, the coils 37A and 37B, which are connected in reverse polarity, are two parts of one monopole antenna assembly. Each coil by itself can be implemented as a standard longitudinal antenna. A monopole antenna can be implemented in another manner.

The polar plot in FIG. 3A shows an example of the antenna sensitivity, demonstrating unidirectional azimuthal selectivity. A combination of the responses of each of the orthogonal transversal-dipole antennas with the response of the monopole antenna can give any of four possible directions covering all quadrants of the transversal plane. Rotation of the drill string while drilling may cause an amplitude modulation of the azimuthally selective response and therefore an amplitude modulation of the NMR relaxation signal (e.g., a CPMG echo train). The amplitude modulation parameters can indicate the azimuthal variations of the NMR properties (e.g., the NMR porosity variations).

The coils 37A and 37B of the example monopole antenna shown in FIG. 3B can be used in combination with transversal-dipole antennas 35 and 36, for example, to achieve azimuthal selectivity. Either of the coils 37A and 37B can also be used as a separate antenna (in addition to or without the transversal-dipole antennas 35, 36), for example, to gain SNR. In some cases, an NMR tool is implemented with a monopole antenna and a longitudinal magnet, without other antennas. For example, the transversal-dipole antennas 35 and 36 may be omitted from the antenna assembly 31 in some cases.

Figure 4A:
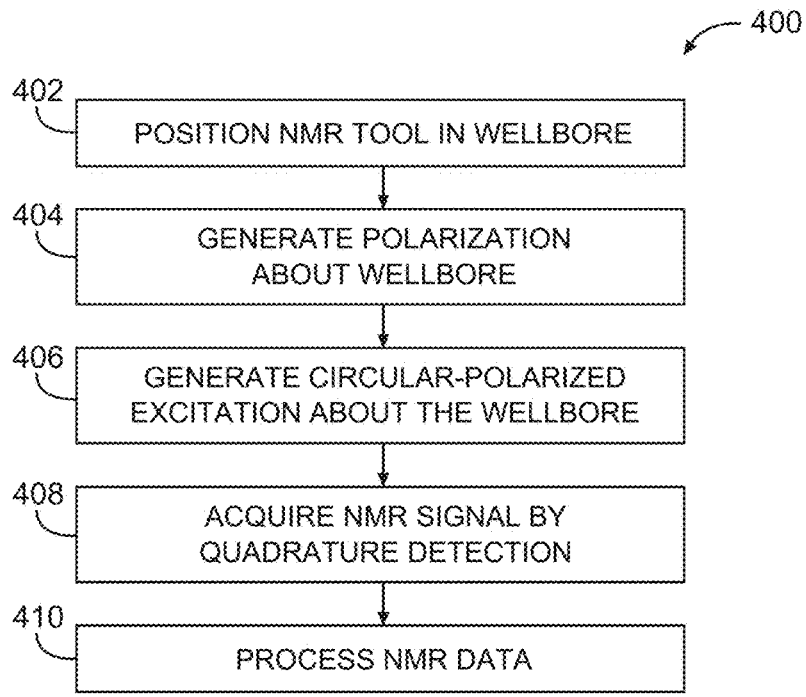
FIG. 4A is a flowchart showing an example technique for obtaining NMR data from a subterranean region, according to various embodiments.
Figure 4B:
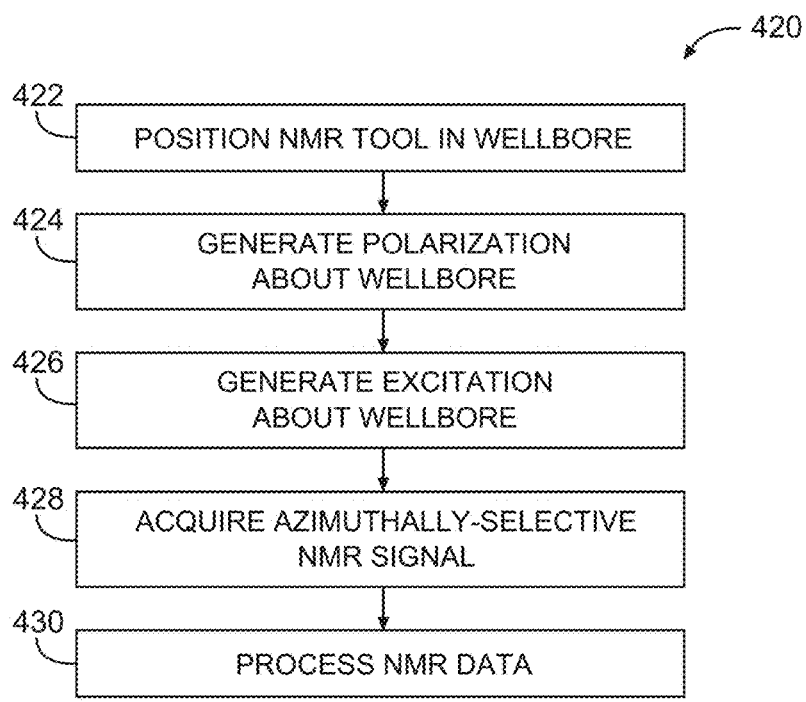
FIG. 4B is a flowchart showing another example technique for obtaining NMR data from a subterranean region, according to various embodiments.

FIG. 4A is a flowchart showing an example technique 400 for obtaining NMR data from a subterranean region, according to various embodiments. FIG. 4B is a flowchart showing another example technique 420 for obtaining NMR data from a subterranean region, according to various embodiments. Each of the processes 400 and 420 can be performed independent of the other, or the processes 400 and 420 can be performed concurrently or in concert. For example, the processes 400 and 420 may be performed in series or in parallel, or one of the processes may be performed without performing the other.

The processes 400 and 420 can be performed by downhole NMR tools such as the example NMR tools 200A, 200B, or 300B shown in FIGS. 2A, 2B and 3B, or by another type of NMR tool. The processes 400 and 420 can be performed by a downhole NMR tool while the tool is disposed within a wellbore during well system operations. For example, the downhole NMR tool can be suspended in the wellbore for wireline logging (e.g., as shown in FIG.

1B), or the downhole NMR tool can be coupled to a drill string for NMR LWD (e.g., as shown in FIG. 1C).

Each of the processes 400 and 420 can include the operations shown in FIGS. 4A and 4B (respectively) or either of the processes can include additional or different operations. The operations can be performed in the order shown in the respective figures or in another order. In some cases, one or more of the operations can be performed in series or parallel, during overlapping or non-overlapping time periods. In some cases, one or more of the operations can be iterated or repeated, for example, for a specified number of iterations, for a specified time duration, or until a terminating condition is reached.

At 402 in the example process 400 shown in FIG. 4A, the NMR tool is positioned in a wellbore. In some cases, the NMR tool includes a magnet assembly to produce a magnetic field in a volume in the subterranean region about the wellbore. The volume can include, for example, all or part of any of the volumes of investigation 17, 21, 24A, 24B, 34 shown in FIG. 2A, 2B or 3B, or another volume of interest. Generally, the NMR tool includes a magnet assembly to polarize nuclear spins in the volume of interest, and an antenna assembly to excite the nuclear spins and to acquire an NMR signal based on the excitation.

At 404, polarization is generated in a volume about the wellbore. The polarization is generated by a static magnetic field, which is produced by the magnet assembly of the NMR tool in the wellbore. The polarization refers to the magnetic polarization of the nuclear spins in the volume. In other words, a portion of the nuclear spins becomes aligned with the static magnetic field, and the volume develops a bulk magnetic moment. In some cases, the static magnetic field is configured (e.g., by the shape and position of the magnet assembly) to produce longitudinal polarization (e.g., parallel to the long axis of the wellbore) or polarization having another orientation.

In some examples, the magnet assembly includes a central magnet (e.g., the central magnet 12 shown in FIGS. 2A, 2B, 3B, or another type of central magnet) and two end piece magnets (e.g., the end piece magnets 11A, 11B shown in FIGS. 2A, 2B, 3B, or another type of end piece magnet). In some cases, the magnets in the magnet assembly are permanent magnets. As shown, for example, in FIG. 2A, the central magnet can be an elongated permanent magnet having a first axial end and a second, opposite axial end, with the first end piece magnet spaced apart from the first axial end of the central magnet, and with the second end piece magnet spaced apart from the second axial end of the central magnet. In some cases, the two end piece magnets have a common magnetic field orientation, and the central magnet has the opposite magnetic field orientation (e.g., such that both end piece magnets have a magnetic field orientation that is orthogonal to the magnetic field orientation of the central magnet).

At 406, circular-polarized excitation is generated in the volume about the wellbore. The circular-polarized excitation is produced in the volume by an antenna assembly. For example, the antenna assembly can be energized by an oscillating current in the radio frequency range which produces a radio-frequency (RF) magnetic field in the volume about the wellbore. Circular polarization is an attribute of using two antennae where the resulting alternating field rotates. In circular polarization the RF field maintains its magnitude, but the orientation rotates around a particular vector. This is in contrast to a single antenna which has a field in one direction (e.g., linear) that grows and shrinks along a line. The RF magnetic field generated by the antenna assembly manipulates the nuclear spins to produce an excited spin state.

In some examples, the antenna assembly includes orthogonal transversal-dipole antennas. The antenna assembly 13 shown in FIGS. 2A and 2B and the antenna assembly 31 shown in FIG. 3B are examples of antenna assemblies that include two orthogonal transversal-dipole antennas. Each antenna 15, 16 in the example antenna assembly 13 can independently produce a transversal-dipole magnetic field, for example, by conducting radio-frequency current. In the examples shown, each transversal-dipole magnetic field has a transverse orientation with respect to the longitudinal axis of the NMR tool. In other words, the transversal-dipole magnetic field is oriented orthogonal to the long axis of the wellbore.

In the example shown, the transversal-dipole magnetic field produced by the antenna 15 is orthogonal to the transversal-dipole magnetic field produced by the other antenna 16. For example, in a Cartesian coordinate system of three mutually-orthogonal directions, the longitudinal axis of the NMR tool can be considered the "z" direction, and the transversal-dipole magnetic fields (produced by the antennas 15, 16) are oriented along the "x" and "y" directions, respectively.

In some implementations, multiple excitations are produced by the NMR tool. For example, in some cases, the circular-polarized excitation is produced in a first sub-volume (e.g., the volume of investigation 21 in FIG. 2B) by the orthogonal transversal-dipole antennas, and excitation having another orientation is produced in second and third sub-volumes (e.g., the volumes of investigation 24A, 24B in FIG. 2B) that are spaced apart from the axial ends of the first sub-volume. The excitation in the second and third sub-volumes can be produced, for example, by a longitudinal-dipole RF field generated by other antenna assemblies (e.g., by antennas 23A and 23B in FIG. 2B). The distinct sub-volumes may be useful for different purposes. For example, the first sub-volume can be elongate (parallel to the long axis of the wellbore), to acquire NMR data from the first sub-volume while the NMR tool moves along the wellbore (e.g., while tripping a drill string). In some cases, the other sub-volumes can be positioned to acquire NMR data for mud filtrate invasion profiling or other applications.

At 408, an NMR signal is acquired by quadrature coil detection. The NMR signal is based on the excitation generated at 406. The NMR signal can be, for example, an echo train, a free induction decay (FID), or another type of NMR signal. In some cases, the acquired NMR data includes $T_1$ relaxation data, $T_2$ relaxation data, or other data. The NMR signal can be acquired by the antenna assembly that produced the excitation or by another antenna assembly. In some cases, an NMR signal can be acquired in multiple sub-volumes.

Quadrature coil detection can be performed by the orthogonal transversal-dipole antennas. Quadrature coil detection can be performed by using two orthogonal coils, each picking up the signal induced by circular polarized nuclear magnetization (the signal in the coils have 90 degree phase difference). Even if during transmission only one coil is used (e.g., producing linear polarized RF magnetic field), the nuclear magnetization can still be circular polarized—by disposing of half of the linear field. Quadrature coil transmission (two orthogonal coils driven by RF currents having 90 degree phase difference) can enable circular polarized excitation, which can help to reduce power consumption compared to a linear polarized excitation in some cases.

Quadrature coil detection can be used, for example, to increase signal-to-noise ratio (SNR) when exciting only one coil (not using circular polarized excitation to simplify hardware), or circular polarization can be used to save power while detecting signals with one coil. In some cases, both circular polarization and quadrature coil detection can be used to save power and increase SNR. In some cases, the use of circular polarization or quadrature coil detection (or both) is efficient when the mutually orthogonal antennas are substantially identical. This is possible in the example magnet/antenna configuration that has a longitudinal dipole magnet and two transversal antennae. Other configurations that have one of the two antennae less efficient than the other, although allowing for mutually orthogonal antennae, may not provide the same advantages in some cases.

At 410, the NMR data are processed. The NMR data can be processed to identify physical properties of the subterranean region or to extract other types of information. For example, the NMR data may be processed to identify density, viscosity, porosity, material content, or other properties of the subterranean region about the wellbore.

At 422 in the example process 420 shown in FIG. 4B, the NMR tool is positioned in a wellbore, and at 424 polarization is generated in a volume about the wellbore. Operations 422 and 424 in FIG. 4B are similar to operations 402 and 404 shown in FIG. 4A. For example, the NMR tool includes a magnet assembly to polarize nuclear spins in the volume of interest, and an antenna assembly to excite the nuclear spins and to acquire an NMR signal based on the excitation. The polarization can be produced at 424 in the manner described with respect to operation 404 of FIG. 4A and by the same type of magnet assembly; or polarization can be produced at 424 in another manner or by another type of magnet assembly.

At 426, excitation is generated in a volume about the wellbore. The excitation is produced in the volume by an antenna assembly. For example, the antenna assembly can be energized by a radio-frequency current, which produces a radio-frequency (RF) magnetic field in the volume about the wellbore. The RF magnetic field generated by the antenna assembly manipulates the nuclear spins to produce an excited spin state. In some instances, the spin state has a higher excitation in a selected azimuthal direction, such that the level of spin excitation varies along a circular (or circumferential) direction about the wellbore, for example, due to an azimuthally-selective RF magnetic field.

In some examples, the antenna assembly includes a transversal-dipole and monopole antenna assembly. The antenna assembly 31 shown in FIG. 3B is an example of an antenna assembly that includes a transversal-dipole and monopole antenna assembly. In the example shown in FIG. 3B, the transversal-dipole and monopole antenna assembly includes two orthogonal transversal-dipole antennas 35 and 36 in a central region, and a monopole antenna that includes a first coil 37A at a first axial end of the transversal-dipole antennas 35 and 36 and a second coil 37B at a second, opposite axial end of the transversal-dipole antennas 35 and 36; the coils 37A and 37B of the monopole antenna are arranged with opposite polarity.

At 428, an azimuthally-selective NMR signal is acquired. The NMR signal is based on the excitation generated at 426. The NMR signal can be, for example, an echo train, a free induction decay (FID), or another type of NMR signal. In some cases, the acquired NMR data includes $T_1$ relaxation data, $T_2$ relaxation data, or other data. The NMR signal can be acquired by the antenna assembly that produced the excitation or by another antenna assembly. In some cases, the NMR signal is acquired by an antenna assembly having azimuthally-selective sensitivity, such as, a transversal-dipole and monopole antenna assembly.

In some implementations, the azimuthally-selective NMR signal is acquired as a combination of multiple NMR signal acquisitions. The signal acquisitions can include, for example, acquisitions by one or more transversal-dipole antennas and one or more monopole antennas. The signals can be combined to enable azimuthally-resolved measurements of the volume about the wellbore. For example, in some cases, a proper combination of the responses of each of the orthogonal transversal-dipole antennas with the response of the monopole antenna can give any of four possible directions covering all quadrants of the transversal plane.

At 430, the NMR data are processed. The NMR data can be processed to identify physical properties of the subterranean region or to extract other types of information. For example, the NMR data may be processed to identify density, viscosity, porosity, material content, or other properties of the subterranean region about the wellbore. In some cases, the NMR data are processed to identify azimuthal variations in the subterranean region about the wellbore. For example, rotating the NMR tool may cause an amplitude modulation of the azimuthally-selective response. The amplitude modulation parameters can indicate the azimuthal variations of the properties affecting the NMR signal (e.g., porosity, density, viscosity, material content, etc.). Further embodiments may be realized.

For example, conventional methods of using NMR-based tools have been discussed in the literature, but the practical implementation of these concepts was not fully developed. More specifically, the following discussion will present various embodiments that provide a practical way to realize multiple sensitive zones along an NMR tool which has central circular polarized transverse antennas and one or more longitudinal magnets.

Figure 5:
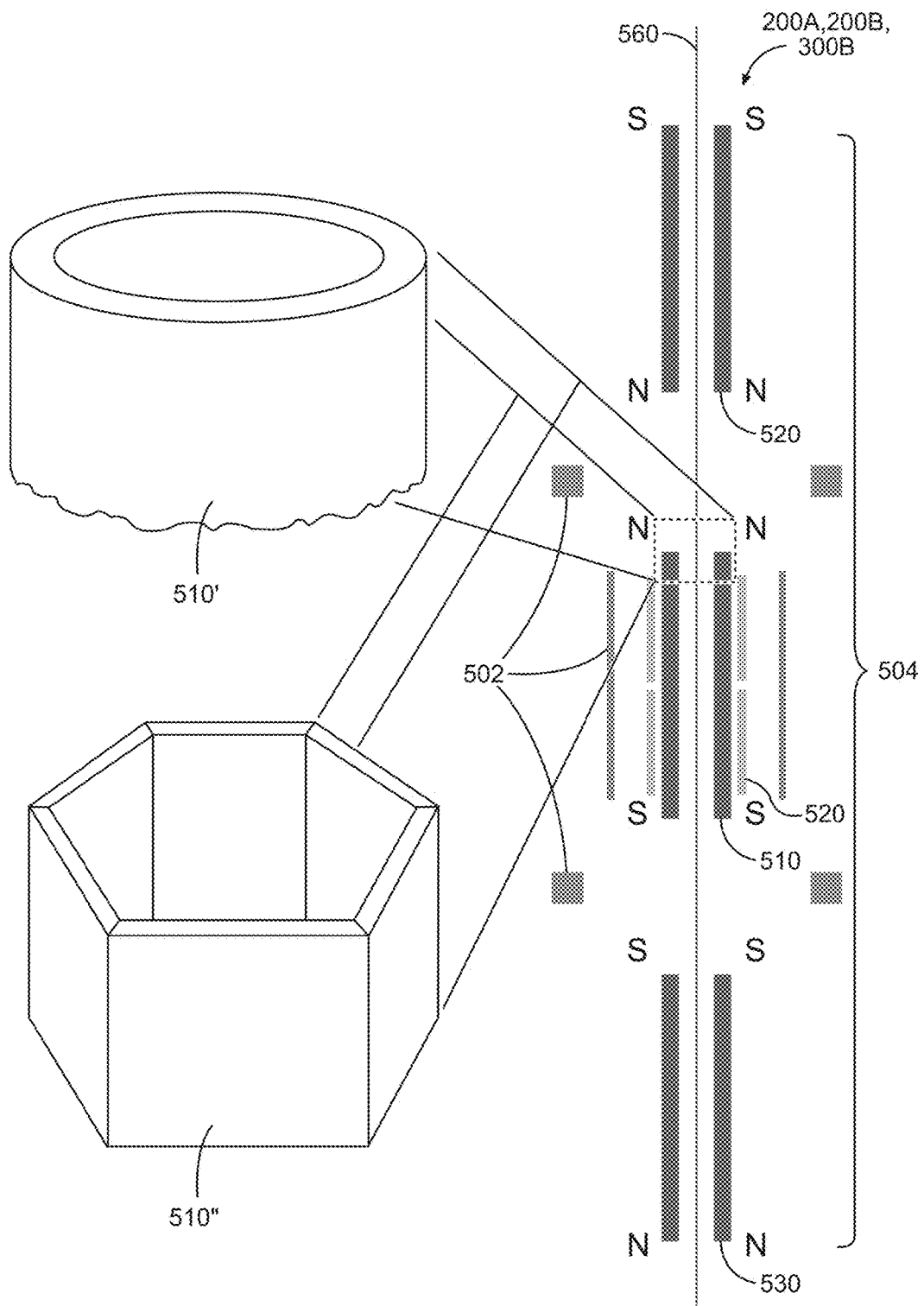
FIG. 5 is a schematic view of an NMR tool configuration, according to various embodiments.
Figure 6:
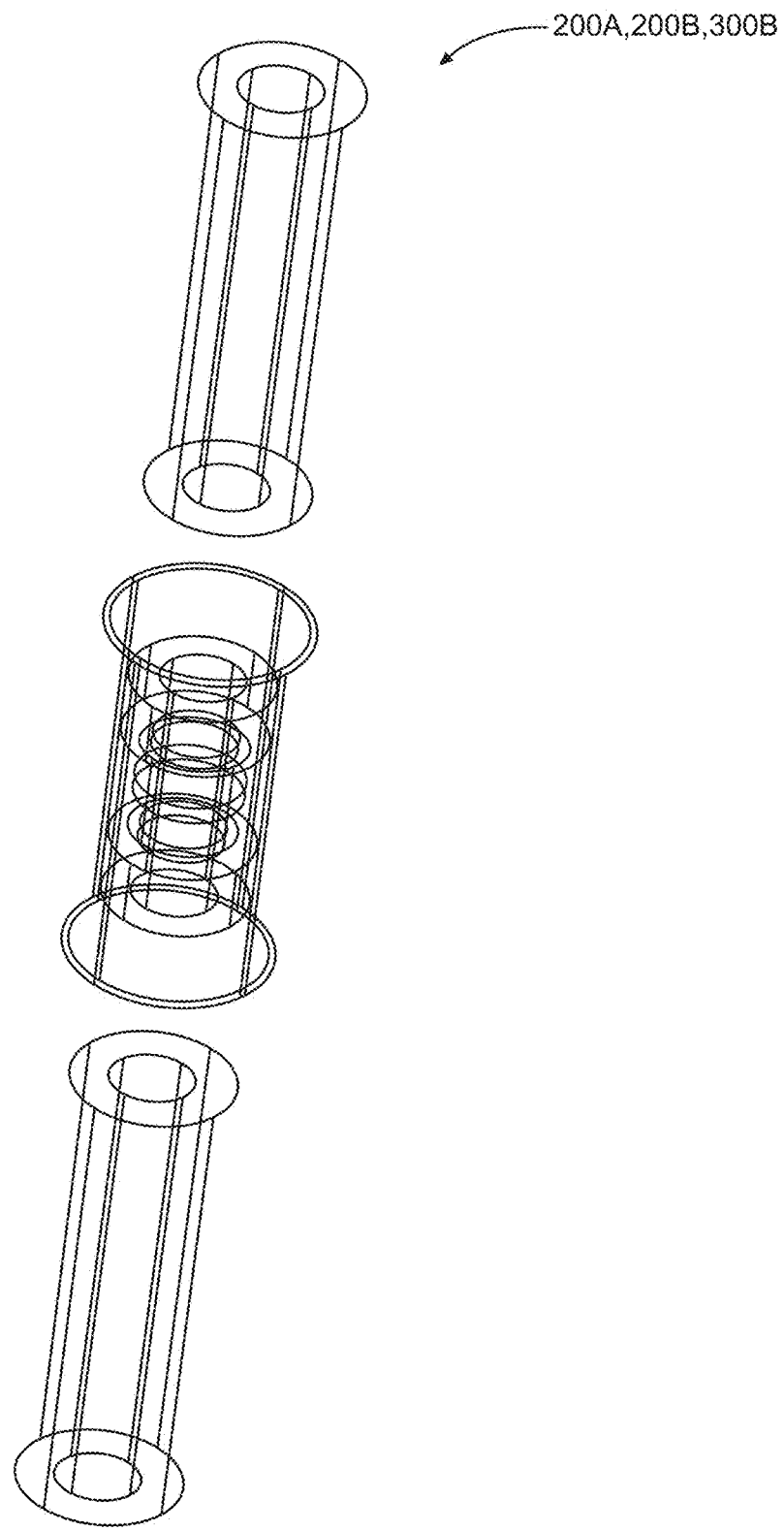
FIG. 6 is a wireframe model view of the NMR tool configuration shown in FIG. 5.

As a mechanism for comparison, FIG. 5 is a schematic view of an NMR tool configuration, according to various embodiments. FIG. 6 is a wireframe model view of the NMR tool configuration shown in FIG. 5. This schematic and wireframe view of tool construction represent an alternative version of the perspective view for the construction shown for NMR tools 200A, 200B, or 300B in FIGS. 2A, 2B and 3B. In these embodiments, tangentially-radial, symmetric magnetic fields 502 are created by a three-section magnet assembly 504 comprising a central magnet 510, a first end piece magnet 520, and a second end piece magnet 530.

A section of the cylindrical central magnet 510 has been broken out in the drawing as ring magnet 510' and pseudo-cylinder magnet 510" to show that although the schematic view provides two-dimensional sections, the magnets (and other component elements of the assembly 404, including the fields 502) are three-dimensional in nature. Thus, magnet configurations henceforth will be represented as a slice cut along the longitudinal axis 560 of a downhole tool. These slices represent a full cylinder as demonstrated in FIGS. 5 and 6, and not demonstrated in the subsequent diagrams as it is understood that all drawing of the magnet assemblies and tools hereafter are represented by a two-dimensional slice.

The NMR sensitive volume in this case is excited using two antennae (not shown, but illustrated as elements 15 and 16 in FIG. 2A, for example) to create the fields 502 utilizing the principles of circular polarization. To shape the fields 502, the magnets 510, 520, 530 and magnetically permeable material 550 can be shaped. The fields 502 can also be shaped by adding shim magnets to the basic configuration shown in FIG. 5, as will be described in subsequent figures.

Figure 7:
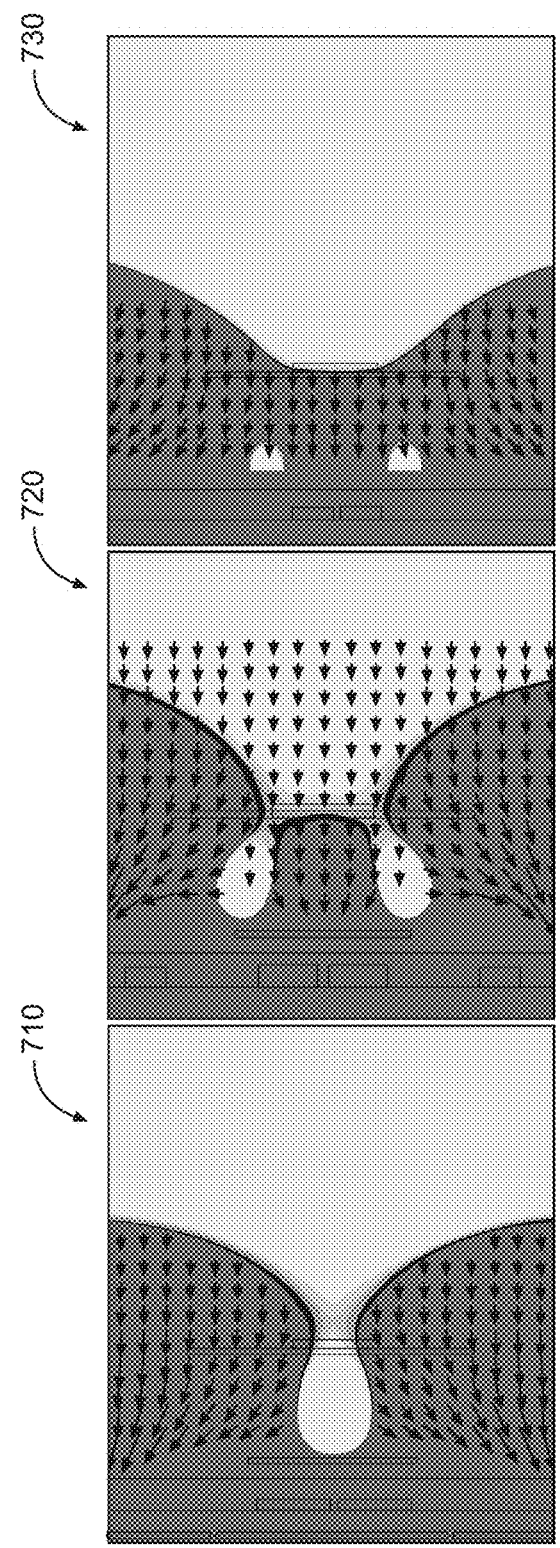
FIG. 7 illustrates side, cut-away views of a portion of a radially-symmetric magnetic field profile, according to various embodiments.

For example, FIG. 7 illustrates side, cut-away views 710, 720, 730 of a portion of a radially-symmetric magnetic field profile, according to various embodiments. The secondary zones can be shaped to form a single saddle point, a double saddle point, a multi-saddle point, or beyond a saddle point. For example, in the views 710, 720, 730 the fields are all radially symmetric. Each view shows a slice radially outward and along the tool's longitudinal axis, where the fields have been shaped to form what is known to those of ordinary skill in the art as a pillow type (e.g., view 710), a butterfly type (e.g., view 720), and a past-saddle-point" type (e.g., view 730).

Secondary zones such as these may be formed using two long sets of magnets where the same pole-sides face each other, perhaps using a Jasper-Jackson design that is known to those of ordinary skill in the art. For example, two long sets of ring magnets having a length of 0.1 m could be spaced about 0.1 m apart, with the Southern poles facing each other. Two long magnets in this position will be called "pole" magnets henceforth. A magnetically permeable material may be placed in the center of this configuration (e.g., see material 550 in FIG. 5). This material has many uses, one of which is shaping a magnetic field. However, using only the three-part configuration shown in FIG. 5, adjusting the magnet lengths, separating the poles, and magnetically permeable material configuration is sometimes not enough to provide the DOI or gradient desired, with respect to the effective NMR sensitive volume. Thus, although shaping the fields 502 is difficult, it can sometimes be accomplished by adding magnetically permeable material over the outside of each of the magnets. This action may be sufficient to focus the antenna field outward and, at the same time, reduce the magnitude of the B1 field towards the magnets. However, this is not always possible.

Figure 8:
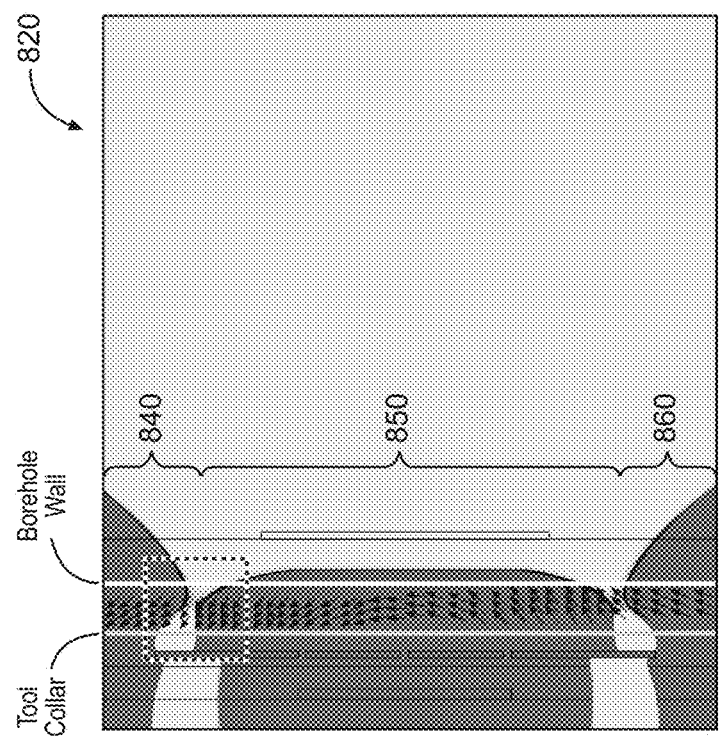
FIG. 8 illustrates side, cut-away views of a portion of a modeled radially-symmetric magnetic field profile, according to various embodiments.
Figure 8:
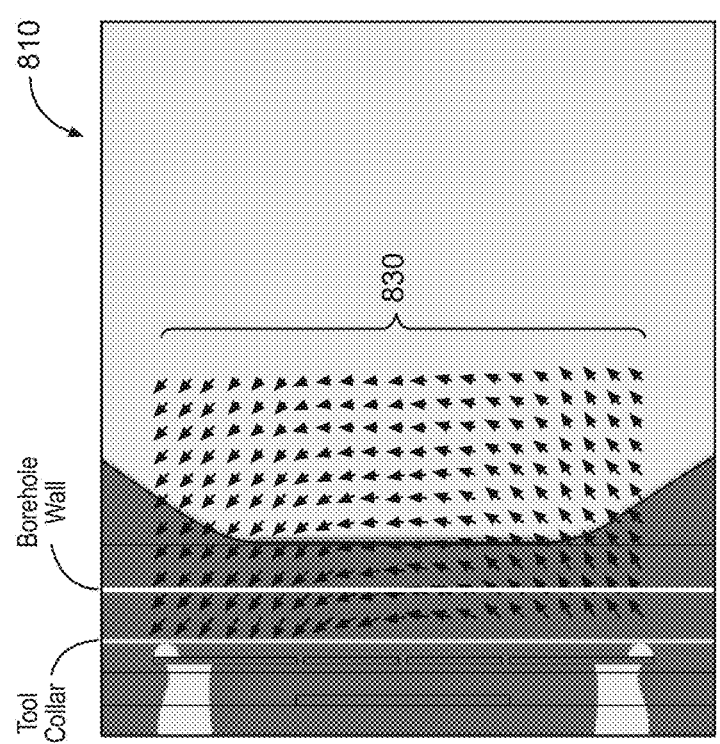

For example, FIG. 8 illustrates side, cut-away views 810, 820 of a portion of a modeled radially-symmetric magnetic field profile, according to various embodiments. In this case, the views 810, 820 correspond to shaping fields using the configuration of FIG. 5. The single active NMR zone 830 is long and deep. When magnet lengths and pole separation are adjusted, and magnetically permeable material are applied to the configuration shown in FIG. 5, three zones 840, 850, 860 exist, at the same frequency. Unfortunately, the saddle point zone 850 falls into the borehole. While this profile may be useful may be useful for measurement in some cases, it is not generally desired.

Figure 9:
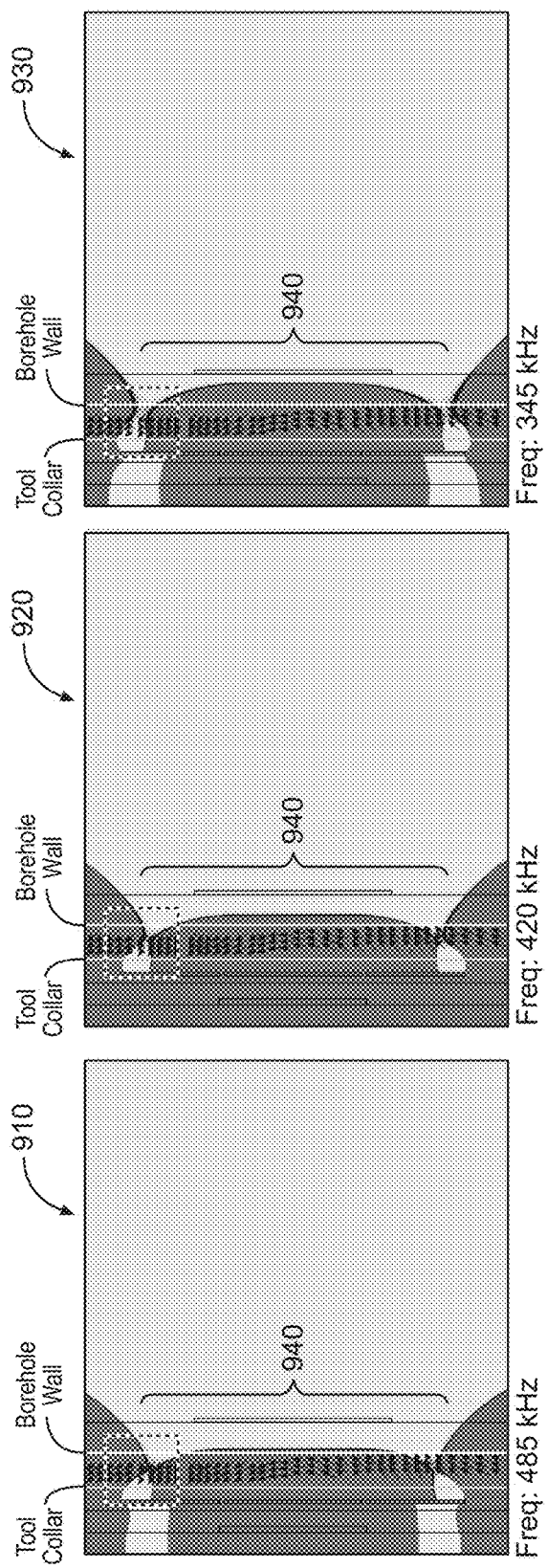
FIG. 9 illustrates side, cut-away views of a portion of a modeled radially-symmetric magnetic field profile, as pole magnets move away from the center, according to various embodiments.

FIG. 9 illustrates side, cut-away views 910, 920, 930 of a portion of a modeled radially-symmetric magnetic field profile, as pole magnets move away from the center, according to various embodiments. Here it can be seen that as the pole magnets are moved further away from the center (i.e., the central magnet in a three-magnet configuration, such as that shown in FIG. 5), the pillow zone 940 moves outward past the borehole wall, and the sensitive volume (spin central or antenna resonant) frequency drops.

Figure 10:
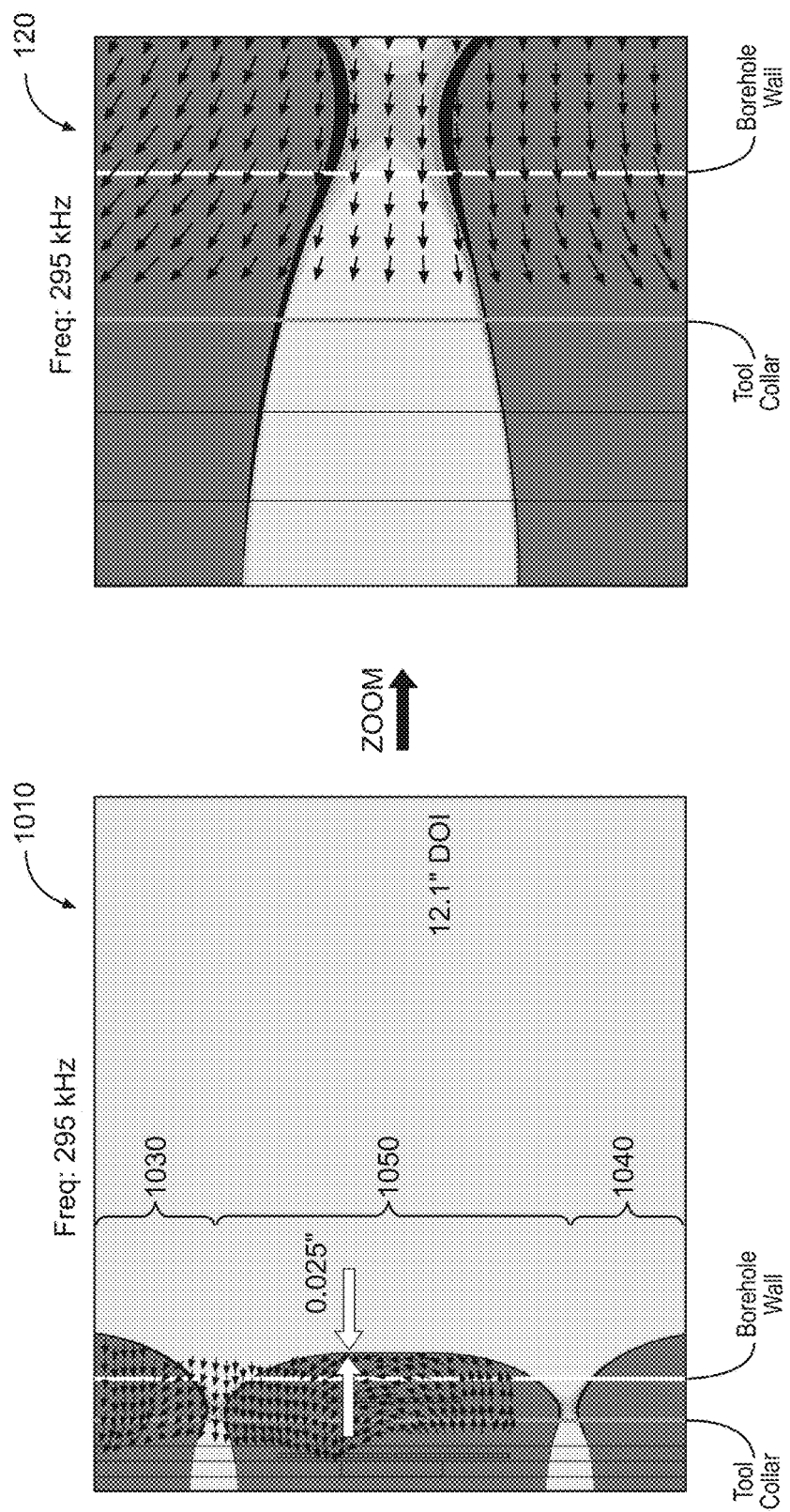
FIG. 10 illustrates side, cut-away views of a portion of a modeled radially-symmetric magnetic field profile, as pole magnets move away from the center, at an operating frequency of 295 kHz, according to various embodiments.
Figure 11:
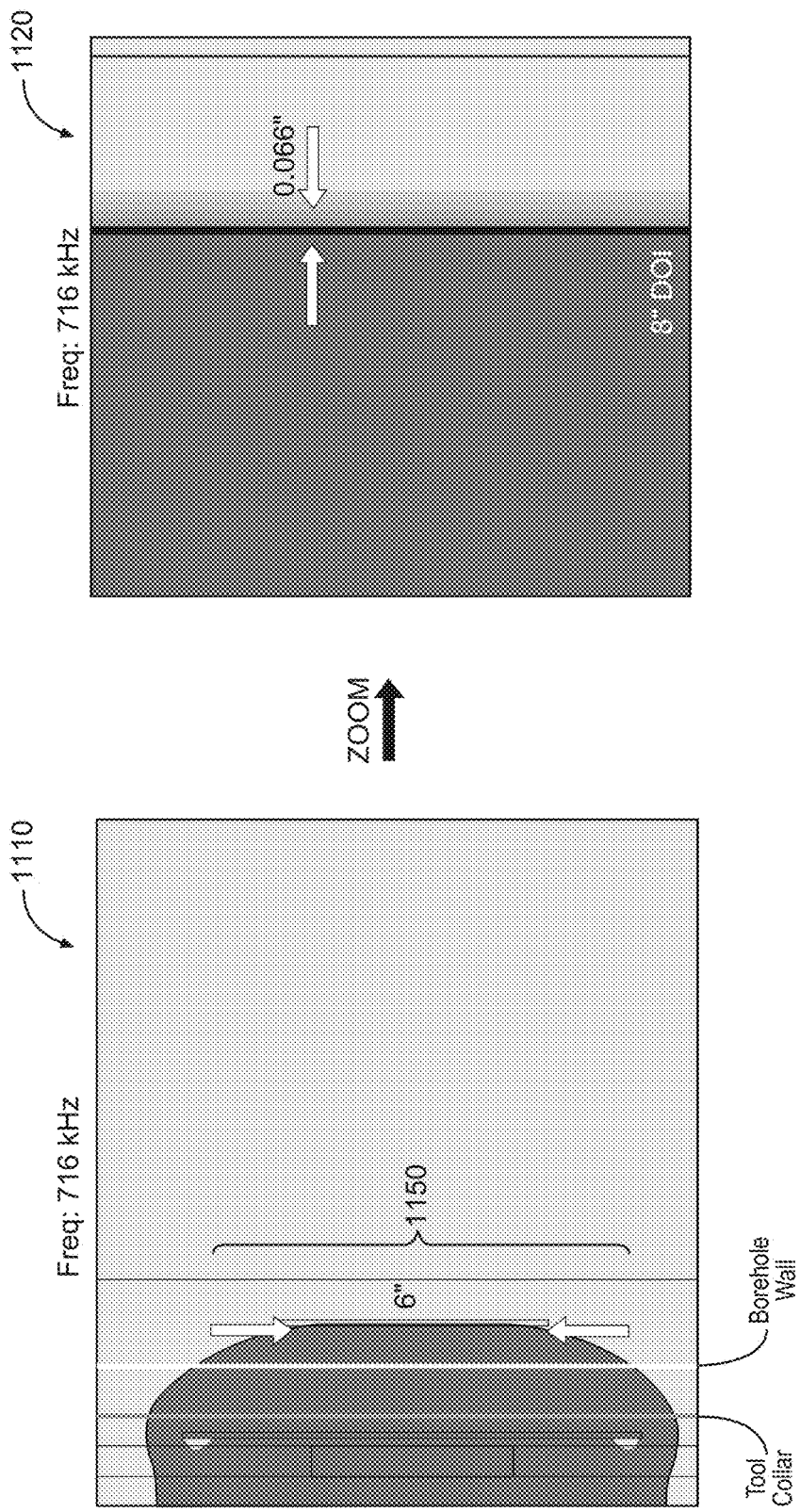
FIG. 11 illustrates side, cut-away views of a portion of a modeled radially-symmetric magnetic field profile, as pole magnets move away from the center, at an operating frequency of 716 kHz, according to various embodiments.

FIG. 10 illustrates side, cut-away views 1010, 1020 of a portion of a modeled radially-symmetric magnetic field profile, as pole magnets move away from the center, at an operating frequency of 295 kHz, according to various embodiments. FIG. 11 illustrates side, cut-away views 1110, 1120 of a portion of a modeled radially-symmetric magnetic field profile, as pole magnets move away from the center, at an operating frequency of 716 kHz, according to various embodiments. These views correspond to increasing the central magnet outside diameter and separating the pole magnets from the central magnet, to create a secondary zone that is radially-directed and past the borehole wall. The total magnet span in this case approach three meters. However, the resulting sensitive volume frequency for many situations would be less than is desirable.

Thus, a three-magnet configuration (shown in FIG. 5) is unlikely to give desirable depths of investigation (see FIG. 8), desirable NMR operational frequency (see FIG. 9), a desirable tool length, and a deep DOI (see FIG. 10) at the same time for the top 1030, bottom 1040, and center 1050 NMR active zones. In practice, with only three magnets, only a single saddle point (i.e., zones 1050, 1150) will arise naturally within the gap between the middle and top/bottom magnets. However, the addition of more magnets and permeable material can help control the type of fields created, along with the total length of the tool, to provide a more desirable result. The following figures demonstrate some non-limiting examples.

Figures 12, 13:
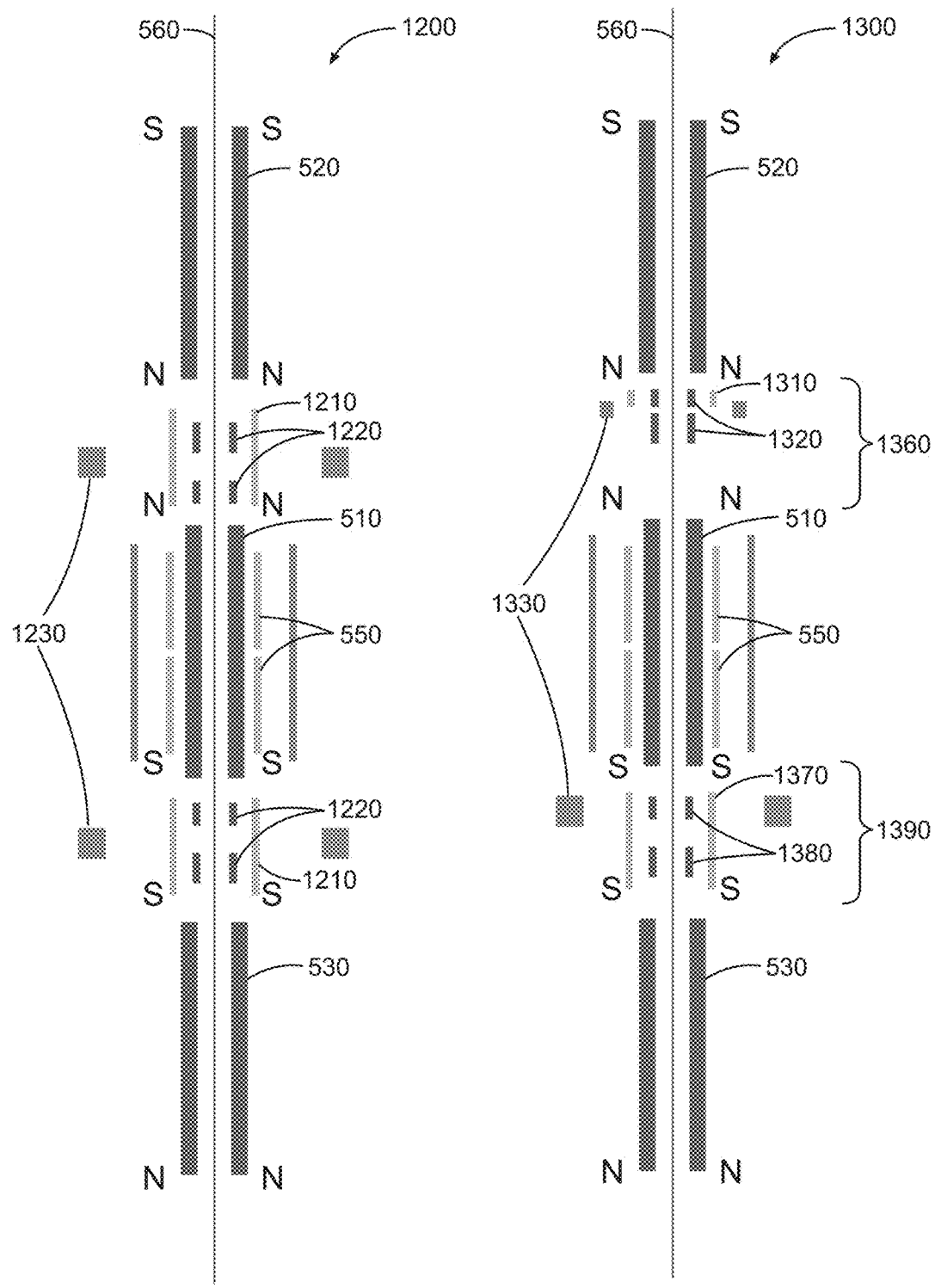
FIGS. 12-13 are schematic views of NMR tool configurations, according to various embodiments.

FIGS. 12-13 are schematic views of NMR tool configurations 1200, 1300, according to various embodiments. Here the configurations 1200, 1300 may include any and all of the elements shown in configurations 200A, 200B and 300B, shown in FIGS. 2A, 2B, and 3C, respectively. In addition, magnetically permeable material 1210, such as ferrite, or Ferrotron 559H soft magnetic composite material available from Fluxtrol, Inc. of Auburn Hills, Mich., and/or one or more shim magnets 1220 are disposed between the central magnet 510 and the first and second end piece magnets 520, 530, respectively. By adding small inner magnets (e.g., magnets 1220) between the central magnet 510 and the end piece magnets 520, 530, a radially (i.e., the dominant field direction) sensitive zone with a deeper and more desirable DOI can be created.

Indeed, many variations are possible. For example, in the tool configuration 1200, the fields 1230 and DOI are symmetrical, due to the symmetrical location and size of the magnetically permeable material 1210 and shim magnets 1220. The ends of the shim magnets 1220 may oppose or align with the end piece magnets 520, 530, and the central magnet 510, depending on the desired field strength and shape. The magnets 510, 520, 530, 1220 may comprise rings (similar to or identical to ring magnet 510' in FIG. 5), rectangular sections (e.g., similar to or identical to the pseudo-cylinder magnet 510" shown in FIG. 5), or some arbitrary shape (e.g., triangular, square, or ellipse).

In some embodiments, the magnets 510, 520, 530, 1220 have a remnant field orientation along the longitudinal axis 560 of the tool. In some embodiments, the remnant field orientation is radially symmetric, and in others, tilted. For example, a pseudo-cylinder (e.g., the cylinder 510" shown in FIG. 5) can be formed via the circular arrangement of several rectangular magnets, of the same or different sizes, around the azimuthal periphery of the tool.

In many embodiments, symmetry is not necessary, nor desirable. Thus, while the configuration 1200 is entirely symmetric, the configuration 1300 is asymmetric. The asymmetry in configuration 1300 stems from the use of different sizes of shim magnets, and different amounts of magnetically permeable material. Thus, the shim magnets 1320 are smaller and the amount of magnetically permeable material 1310 adjacent to them is less in the upper portion 1360 of the configuration 1300, whereas the shim magnets 1380 are larger and the amount of magnetically permeable material 1370 adjacent to them is greater in the lower portion 1390 of the configuration 1300. The result is that the fields 1330 for configuration 1300 are different, with a different DOI. Whereas the fields 1230 are the same, with the same DOI.

In either configuration 1200, 1300, one or more antennae (e.g., antennae 15 and 16 shown in FIG. 2A, or antennae 35, 26, 37A, 37B in FIG. 3B) can be disposed over the magnetically permeable material 550. In some embodiments, copper is disposed between one or more antennae (e.g., antennae 15 and 16 shown in FIG. 2A, or antennae 35, 26, 37A, 37B in FIG. 3B), and the magnetically permeable material 550. These antennae and the copper are not shown in FIGS. 12 and 13, so as not to obscure the appearance of other elements; to view the application of these features, the reader is referred to FIG. 15.

Figure 14:
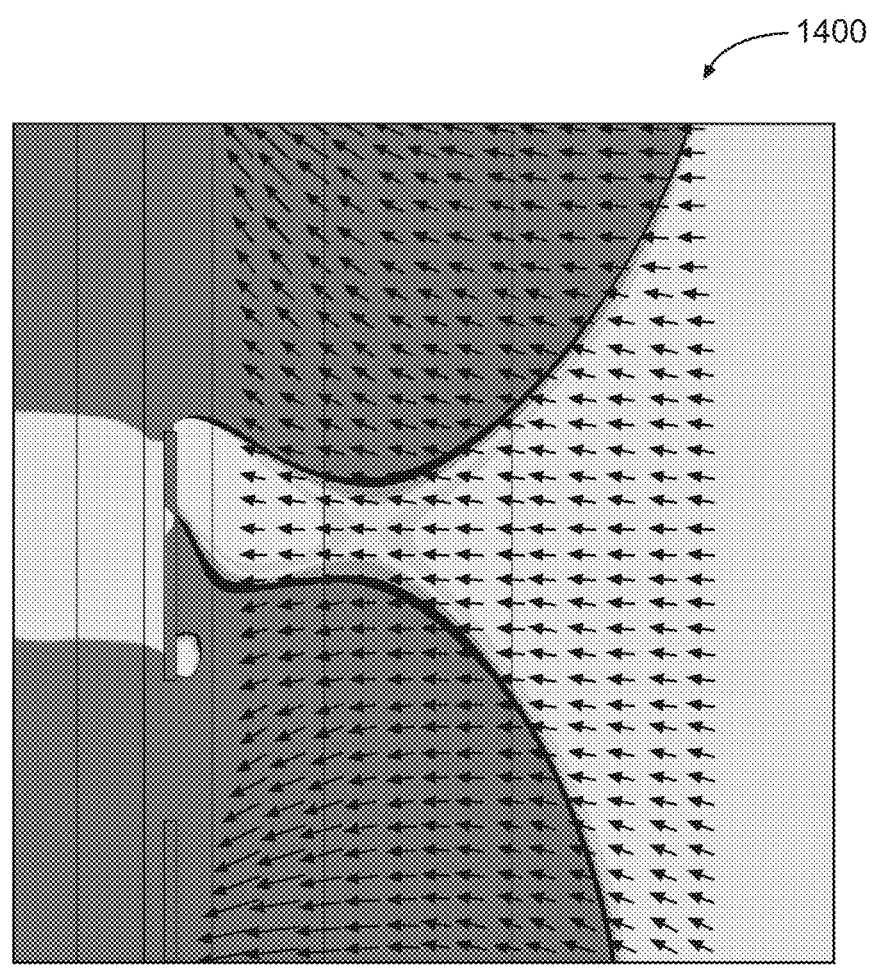
FIG. 14 illustrates a field profile of the pillow zone in the magnetic field created by the addition of magnetically permeable material to the tool configuration, according to various embodiments.

FIG. 14 illustrates a field profile 1400 of the pillow zone in the magnetic field created by the addition of magnetically permeable material to the tool configuration, according to various embodiments. Here the pillow zone is created only by the addition of magnetically permeable material between the central magnet and one of the end piece magnets. In addition to magnets, NMR tools constructed according to various embodiment may be operated with a magnetically permeable material between the magnets and one or more antennae (see FIG. 15). This construction helps reduce antenna field penetration of the magnet, which might cause ringing. This construction also helps to focus the B1 magnetic field outward into the formation, to increase the available SNR. This configuration is essentially the same as configuration 1200 of FIG. 12, with the magnetically permeable material 1210 present, and without any shim magnets 1220. The resulting radial pillow zone occurs at a frequency of 205 kHz, with a total tool length of about 3 m, with the pole magnets (end piece magnets spread further apart than is shown in FIG. 12), to obtain a larger DOI.

Figure 15:
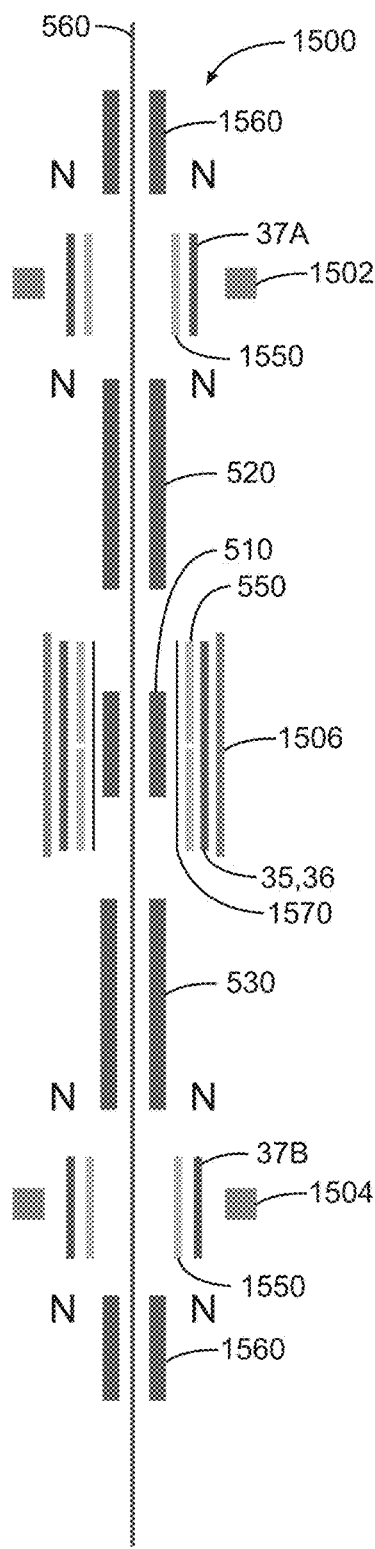
FIGS. 15-16 are schematic views of NMR tool configurations, according to various embodiments.
Figure 16:
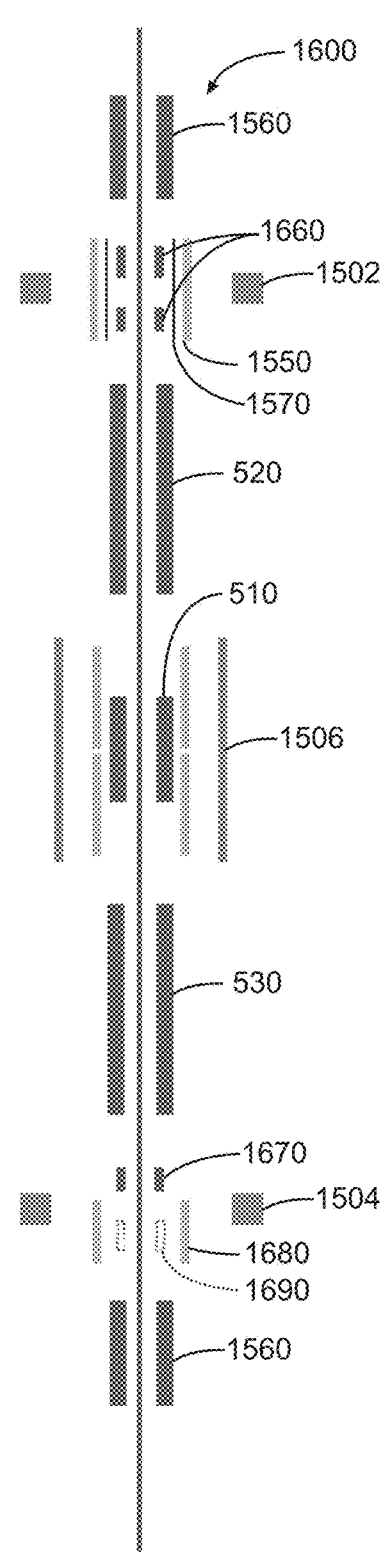
Figure 17:
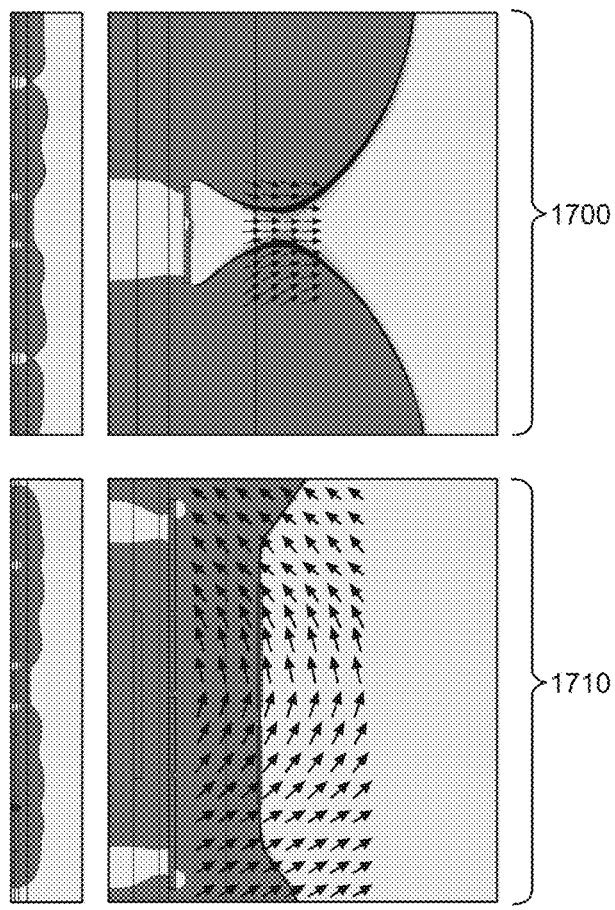
FIG. 17 illustrates symmetric field profiles of the magnetic fields that correspond to the NMR tool configurations of FIGS. 15-16, according to various embodiments.

FIGS. 15-16 are schematic views of NMR tool configurations 1500, 1600, according to various embodiments. FIG. 17 illustrates symmetric field profiles 1700, 1710 of the magnetic fields that correspond to the NMR tool configurations of FIGS. 15-16, according to various embodiments.

To this point, the advantage of using additional shim magnets 1560, disposed at the outer ends of the end piece magnets 520, 530 has not been discussed. When this embodiment is implemented, as shown in FIGS. 15, 16, 18, and 20, instead of creating second and third sensitive zones (shown as components of the fields 502 in FIG. 5) between the two end piece magnets of a three-magnet configuration (shown as magnets 510, 520, 530 in FIG. 5), the second and third zones 1502, 1504 are created outside of the three-magnet configuration 510, 520, 530, while the central zone 1506 remains located between the two end piece magnets 520, 530. In another embodiment, shim magnets 1560 are disposed adjacent to only one of the end piece magnets (e.g., magnet 520). This option provides only two sensitive zones 1502, 1506.

In FIG. 15, the additional shim magnets 1560 have been added in a symmetric fashion, with their polar magnetization in opposition to that of the proximal end piece magnets 520, 530. Disposed between the shim magnets 1560 and the end piece magnets 520, 530 is a magnetically permeable material 1550. One or more antennae 37A, 37B may be disposed over the magnetically permeable material 1550. As was the case in prior embodiments, antennae 35, 36 may also be disposed over the magnetically permeable material 550. In each case where an antenna is disposed over magnetically permeable material, copper 1570 may be placed in-between the antenna and the magnetically permeable material. As can be seen in FIG. 16, additional shim magnets 1660 can be added to the configuration shown in FIG. 15 to fine-tune the sensitive field distribution, as well as the DOI. Any number of shim magnets 1560, 1660 can be used, but in many cases, two such magnets are sufficient to achieve inspection objectives. The configurations shown in FIGS. 15 and 16 permit the central sensitive zone 1506 to remain symmetrically uncompromised.

Again, symmetric configurations, as shown in FIGS. 15-16, may be useful in many applications. In others, an asymmetric distribution of the sensitive volumes may be desired. Thus, the configuration in FIG. 16 allows at least two types of asymmetry, if desired. In the first type, shim magnets 1660 have been added radially beneath the magnetically permeable material 1550. In the second type, the shim magnets 1670 have been added longitudinally between the end piece magnet 530 and the magnetically permeable material 1680. Still more shim magnets 1690 may be added, perhaps underneath the magnetically permeable material 1680. The shim magnets 1660, 1670, 1690 can be added to provide symmetric zones 1502, 1504, or asymmetric zones (e.g., see FIG. 18), as desired.

Thus, some embodiments (e.g., symmetrical) provide the same DOI for each of the outer sensitive zones 1502, 1504. Some embodiments (e.g., asymmetrical) provide a different DOI for each of the outer sensitive zones 1502, 1504. With the latter, different depths of investigation (DOIs) can be provided using the same tool. For any sensitivity zone, any number of frequencies can be used. Saddle point and past saddle point regions might make use of a single antenna if this embodiment is used.

Figure 18:
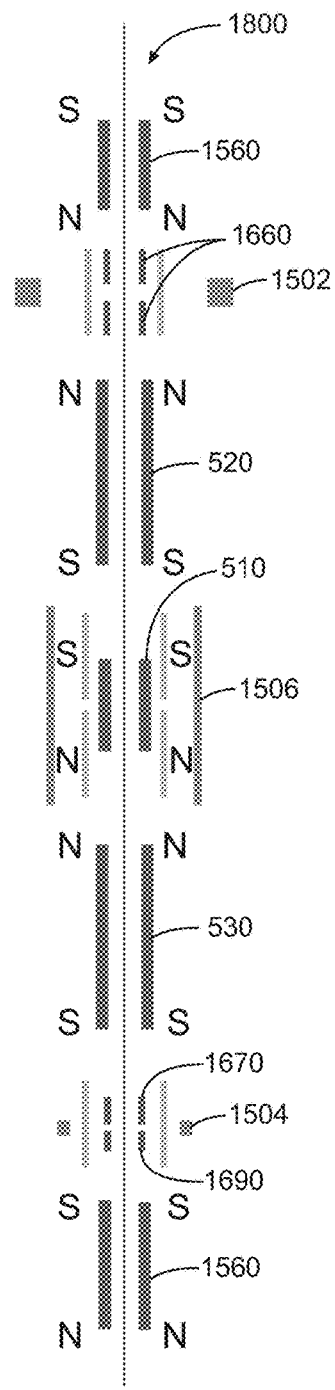
FIG. 18 is a schematic view of an NMR tool configuration, according to various embodiments.
Figure 19:
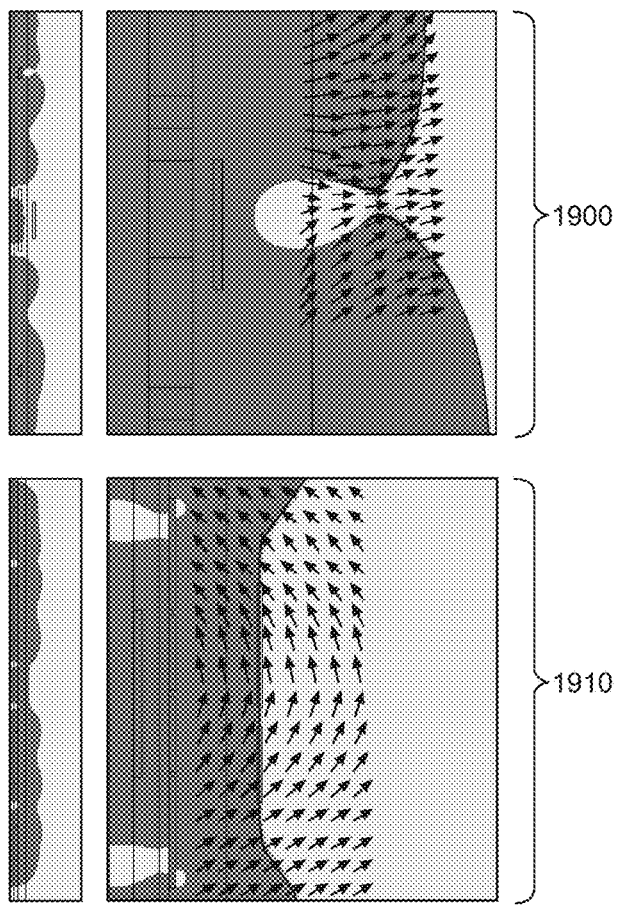
FIG. 19 illustrates asymmetric field profiles of the magnetic fields that correspond to the NMR tool configuration of FIG. 18, according to various embodiments.

FIG. 18 is a schematic view of an NMR tool configuration 1800, according to various embodiments. FIG. 19 illustrates asymmetric field profiles 1900, 1910 of the magnetic fields that correspond to the NMR tool configuration of FIG. 18, according to various embodiments. In this case, an asymmetric configuration 1800 is employed, by using shim magnets 1660 that are larger at one end of the tool, and shim magnets 1670, 1690 that are smaller at the other end of the tool, providing larger and smaller sensitive volumes 1502, 1504, respectively. To maintain an axially-symmetric sensitive zone 1506 in this configuration 1800, the central and/or end piece magnets 510, 520, 530 may need to be adjusted in size.

Figure 20:
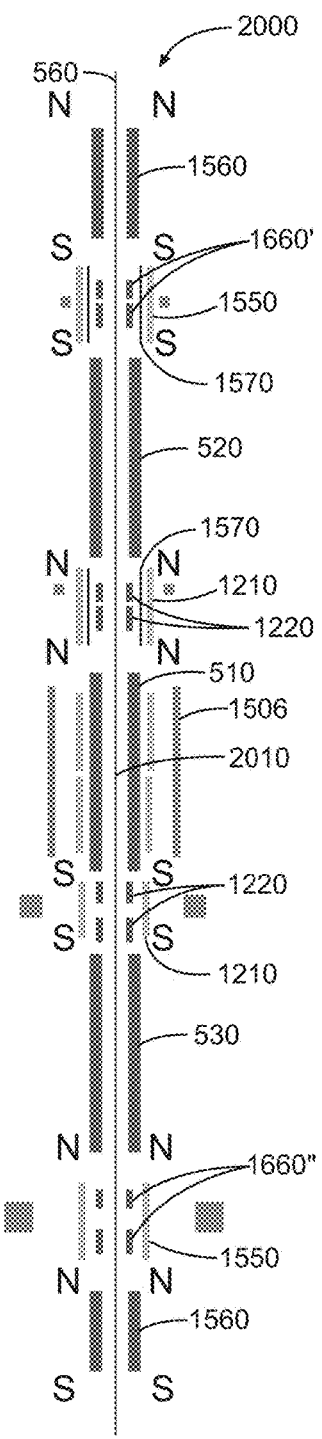
FIG. 20 is a schematic view of an NMR tool configuration, according to various embodiments.

FIG. 20 is a schematic view of an NMR tool configuration 2000, according to various embodiments. Here, the configurations 1200 (from FIG. 12) and 1800 (from FIG. 18) have been combined, with multiple shim magnets 1220 disposed longitudinally between the central magnet 510 and each of the end piece magnets 520, 530. Additional shim magnets 1660 have also been longitudinally disposed between the end piece magnets 520, 530 and shim magnets 1560. The end result is symmetric, but other embodiments are not to be so limited, so the multiple DOIs can be obtained using a single tool configuration. Still further pairs of shim magnets can be used to extend the longitudinal length of configuration 2000, or any other configuration described herein. There is no theoretical limit to the amount of extension, and the number of sensitive zones that are created—but practical limitations on the length of the tool may exist.

Figure 21:
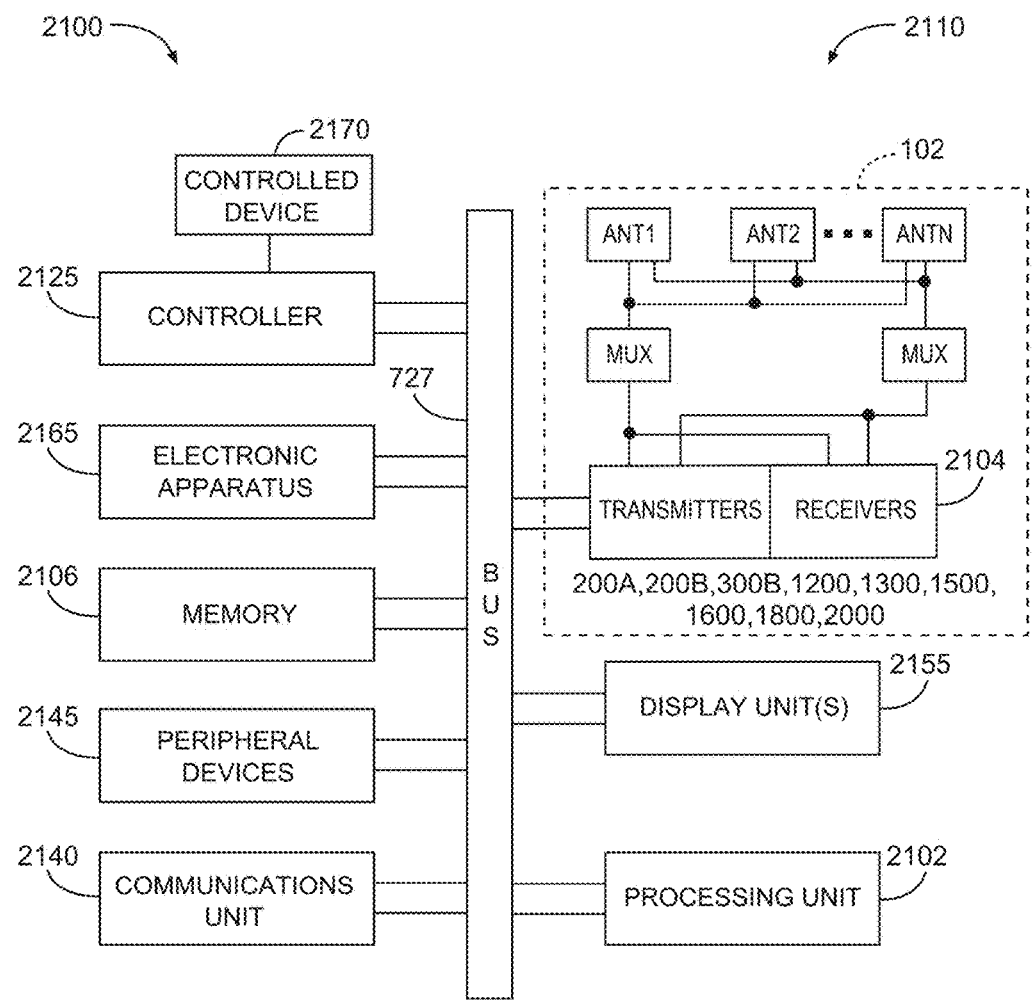
FIG. 21 is a block diagram of apparatus and systems according to various embodiments.

FIG. 21 is a block diagram of apparatus 2110 and systems 2100 according to various embodiments. Here, it can be seen that the system 2100 may include a controller 2125 to interface with a controlled device 2170, such as a geosteering unit, and/or a user display or touch screen interface, which may be included within, or separated from, display units 2155. The system 2100 may further include a number of sensors downhole, including antennae ANT1, ANT2, . . . ANTN as part of the apparatus 2110, which may comprise a downhole tool 102, similar to or identical to the tool 102 shown in prior figures (e.g., FIGS. 1A, 1B, 1C). The apparatus 2110 may thus comprise a downhole tool 102 constructed according to any of the configurations 200A, 200B, 300B, 1200, 1300, 1500, 1600, 1800, 2000, shown in FIGS. 22A, 2B, 3B, 12, 13, 15, 16, 18, and 20 respectively. The apparatus 2110 may further comprise transmitters and/ or receivers (together transceivers 2104), which may be located on the apparatus 2110, or at a surface location, remote from the apparatus 2110. When constructed in this manner, the system 2100 can receive measurements and other data (e.g., corresponding to NMR measurements in a geological formation) to be processed according to various methods described herein.

The processing unit 2102 can be coupled to the transceivers 2104 to obtain measurements from the antennae ANT1, ANT2, . . . , ANTN, among others. The processing unit 2102 may be part of a surface workstation or attached to a downhole tool 102 housing, as part of the apparatus 2110.

The logging system 2100 can include a controller 2125, other electronic apparatus 2165, and a communications unit 2140. The controller 2125 and the processing unit 2102 can be fabricated to operate the antennae ANT1, ANT2, . . . , ANTN to acquire measurement data, such as signals representing sensor measurements, perhaps resulting from NMR excitation of the surrounding formation.

Electronic apparatus 2165 (e.g., electromagnetic sensors, current sensors) can be used in conjunction with the controller 2125 to perform tasks associated with taking measurements downhole. The communications unit 2140 can include downhole communications in a drilling operation. Such downhole communications can include telemetry.

The system 2100 can also include a bus 2127 to provide common electrical signal paths between the components of the system 2100. The bus 2127 can include an address bus, a data bus, and a control bus, each independently configured. The bus 2127 can also use common conductive lines for providing one or more of address, data, or control, the use of which can be regulated by the controller 2125.

The bus 2127 can include instrumentality for a communication network. The bus 2127 can be configured such that the components of the system 2100 are distributed. Such distribution can be arranged between downhole components such as the transceivers 2104 and components that can be disposed on the surface of a well. Alternatively, several of these components can be co-located, such as on one or more collars of a drill string, of which the tool 102 forms a part.

In various embodiments, the system 2100 includes peripheral devices that can include displays 2155, additional storage memory, or other controlled devices 2170 that may operate in conjunction with the controller 2125 or the processing unit 2102. The display 2155 can display diagnostic and measurement information for the system 2100, based on the signals generated according to embodiments described above.

In an embodiment, the controller 2125 can be fabricated to include one or more processors. The display 2155 can be fabricated or programmed to operate with instructions stored in the processing unit 2102 (for example in the memory 2106) to implement a user interface to manage the operation of the system 2100, including any one or more components distributed within the system 2100. This type of user interface can be operated in conjunction with the communications unit 2140 and the bus 2127. Various components of the system 2100 can be integrated with the bottom hole assembly shown in FIG. 1C, which may in turn be used to house the magnets, magnetically permeable material, antennae ANT1, ANT2, . . . , ANTN, etc. as shown in the various configurations 200A, 200B, 300B, 1200, 1300, 1500, 1600, 1800, 2000 described herein, such that the operations and processing identical to or similar to the methods discussed previously, and those that follow, can be conducted. Thus, various embodiments may be realized.

For example, referring now to FIGS. 1-21, it can be seen that in some embodiments, an apparatus 2110 comprises a downhole tool 102 attached to a magnet assembly that includes a central magnet 510 in-between two end piece magnets 520, 530, and one or more shim magnets 1220 with magnetically permeable material 1210 located in-between the central magnet 510 and one of the end piece magnets 520, 530 (e.g., see FIG. 12). The magnetically permeable material 1210 can be disposed over a magnet 1220, at the same longitudinal location as the magnet, as shown in FIG. 12, or as shown in FIG. 15, the magnetically permeable material 1550 may be longitudinally offset from the location of the shim magnet 1560. In some embodiments, the magnetically permeable material 550 is disposed over the central magnet 510, and the magnetically permeable material 12010 is also disposed over the shim magnets 1220, so that the longitudinal location of the magnetically permeable material 1210 and the respective shim magnets 1220 is approximately the same (e.g., see FIG. 12). In some embodiments, the magnetically permeable material 550 is disposed over the central magnet 510, and the magnetically permeable material 1550 is also longitudinally offset from the shim magnets 1560 (exposing the shim magnets 1560 directly to the formation), so that the longitudinal location of the magnetically permeable material 1550 and the respective shim magnets 1560 are different (See FIG. 15).

Thus, in some embodiments, an apparatus 2110 comprises a magnet assembly to produce a magnetic field 1230 in a volume in a geological formation, the magnet assembly attached to a downhole tool 102, with the magnet assembly comprising a central magnet 510 having a first axial end and a second, opposite axial end; a first end piece magnet 520 spaced apart from the first axial end of the central magnet 510; and a second end piece magnet 530 spaced apart from the second axial end of the central magnet 510. The apparatus 2110 further comprises at least one first shim magnet 1220 or 1320 longitudinally disposed between the central magnet 510 and the first end piece magnet 520, the first shim magnet 1220 or 1320 disposed adjacent to or at least partially surrounded by a first magnetically permeable material 1210 or 1310, respectively, the first shim magnet to shape a first static magnetic field sub-volume 1230, 1330 provided by the central magnet 510 and the first end piece magnet 510.

Copper can be used to shield the central magnet and/or shim magnets from the RF antenna pulses. Thus, in some embodiments, the apparatus 2110 comprises copper 1570 radially disposed between the first shim magnet 1220 and the first magnetically permeable material 1210, or between the central magnet 510 and central magnetically permeable material 550.

Shim magnets can be formed as integral rings, or separate elements that combine to form a ring-like structure. Thus, in some embodiments, the at least one first shim magnet comprises multiple unitary ring-shaped elements (e.g., in ring 510') and/or a series of rectangular elements shaped to form a ring (e.g., in ring 510").

A second shim magnet can be added, to mirror the location of the first shim magnet along the longitudinal axis of the tool. Additional magnetically permeable material may be disposed adjacent to or at least partially surrounding the second shim magnet. Thus, in some embodiments, the apparatus 2110 comprises at least one second shim magnet 1670 disposed between the central magnet 510 and the second end piece magnet 530, the second shim magnet 1380 disposed adjacent second magnetically permeable material 1370 or at least partially surrounded by the second magnetically permeable 1370 material and copper 1570 (not shown in FIG. 13, but see copper 1570 disposed between the magnets 1220 and magnetically permeable material 1210 in FIG. 20).

Additional sets of shim magnets, and magnetically permeable material, can be added to symmetrically and outwardly extend the pattern set by the first and second shim magnets, to whatever distance is desired. Thus, in some embodiments, the apparatus 2110 comprises at least one set of additional shim magnets 1660 adjacent to or at least partially surrounded by additional magnetically permeable material 1550, to outwardly extend an arrangement of the at least one first and second shim magnets 1220, and the first and second magnetically permeable material 1210 in a symmetrical fashion along a longitudinal axis 560 of the tool.

The first and second shim magnets and/or the first and second magnetically permeable material can be assembled with relative size differences to enable different depths of investigation. Thus, in some embodiments, geological formation depths of inspection associated with the first shim magnet 1320 and the second shim magnet 1380 are different.

In most embodiments, the central and end piece magnets define magnetic fields that have an orthogonal orientation. Thus, in some embodiments, the central magnet 510 defines a first magnetic field orientation, and the first and second end piece magnets 520, 530 each define a second magnetic field orientation that is substantially orthogonal to the first magnetic field orientation.

The central and end piece magnets may comprise permanent magnets, electromagnets, and other kinds of magnets. Thus, in some embodiments, at least one of the central magnet 510 or the first and second end piece magnets 520, 530 comprise one or more permanent magnets.

The apparatus 2110 may include one or more antennas that can be used to detect an NMR response from one or more magnetic fields defined by the magnets. Thus, in some embodiments, the central magnet 510 and the first and second end piece magnets 520, 530 define an overall static magnetic field volume that comprises multiple distinct sub-volumes 1502, 1504, 1506, the multiple distinct sub-volumes 1502, 1504, 1506 including the first static magnetic field sub-volume 1506 that is elongate in a first direction parallel to a longitudinal axis of the tool 560, the magnetic field in the first static magnetic field sub-volume 1506 being substantially uniformly oriented in the first direction, the apparatus further comprising: antennas 35, 36, 37A, 37B located at respective locations along the longitudinal axis 560, each of the antennas 35, 36, 37A, 37B to detect a nuclear magnetic resonance response from a respective one of the distinct sub-volumes 1502, 1504, 1506 when the antennas 35, 36, 37A, 37B are operating.

The magnetically permeable material may be selected to have a relatively low conductivity, so that losses in the material are less than those in the antennas and the formation. Thus, in some embodiments, conductivity of the first magnetically permeable material 550 is selected to reduce losses in the magnetically permeable material 550 to less than expected losses in the antennas 35, 36, 37A, 37B or the geological formation to be investigated.

Antennas in the apparatus 2110 may comprise a variety of types, such as one or more transversal-dipole antennas to produce circular-polarized excitation in the magnetic field volume, or perhaps to acquire a response from the magnetic field volume by quadrature coil detection. Copper can be disposed over the central magnet, with magnetically permeable material over the copper, and under the antenna(s). Thus, in some embodiments, the apparatus 2110 further comprises an antenna assembly 35, 36 comprising a transversal-dipole antenna 35 disposed over the central magnet 510, with copper 1570 and central magnetically permeable material 550 disposed between the central magnet 510 and the antenna assembly 35, 36.

In some embodiments, an apparatus 2110 comprises a downhole tool 102 that is attached to a magnet assembly that includes a central magnet 510 in-between two end piece magnets 520, 530, with magnetically permeable material 1210 located in-between the central magnet 510 and a first end of one of the end piece magnets 520, 530, and one or more shim magnets 1560 located next to a second end of one of the end piece magnets 520, 530 (e.g., see FIG. 20). Therefore, in some embodiments, an apparatus 2110 comprises a magnet assembly to produce a magnetic field 1506 in a volume in a subterranean region, the magnet assembly comprising a central magnet 510 having a first axial end and a second, opposite axial end; a first end piece magnet 520 having a proximal end and a distal end, the proximal end spaced apart from the first axial end of the central magnet 510; and a second end piece magnet 530 spaced apart from the second axial end of the central magnet 510; at least one first shim magnet 1560 spaced apart from the distal end of the first end piece magnet 520. The apparatus 2110 further comprises a downhole tool 102 attached to the magnet assembly, further comprising first magnetically permeable material 1550 disposed adjacent to or at least partially surrounding a longitudinal axis 560 of the tool, the first magnetically permeable material 1550 disposed between the first end piece magnet 520 and the first shim magnet 1560.

The magnetically permeable material can be used to surround additional shim magnets. Thus, in some embodiments, the apparatus 2110 further comprises at least one second shim magnet 1560 disposed adjacent to or at least partially surrounded by the first magnetically permeable material 1550.

Copper may be placed between the magnetically permeable material and additional shim magnets. Thus, in some embodiments, the apparatus 2110 further comprises copper 1570 disposed between the magnetically permeable material and the at least one second shim magnet.

The apparatus 2110 may include a symmetrical, mirrored arrangement of additional magnetic and magnetically permeable elements. Thus, in some embodiments, the apparatus 2110 further comprises at least one second shim magnet 1560 spaced apart from a distal end of the second end piece magnet 530 and second magnetically permeable material 1550 disposed between the second end piece magnet 530 and the second shim magnet 1560, to mirror an arrangement of the first shim magnet 1560 and the first magnetically permeable material 1550 about a center point 2010 of the central magnet 510.

The apparatus 2110 may include an asymmetric arrangement of additional magnetic and magnetically permeable elements. Thus, in some embodiments, the apparatus 2110 further comprises at least one second shim magnet 1220 disposed between the central magnet 510 and the second end piece magnet 530 and second magnetically permeable material 1210 disposed adjacent to or at least partially surrounding the at least one second shim magnet 1220.

In some embodiments, a system 2100 comprises a tool 102 that comprises magnetically permeable material 1310, 1370, and shim magnets 1320 located inside and/or outside of the junction between the central magnet 510 and end piece magnets 520, 530 (e.g., see FIG. 13). The tool 102 is coupled to a transmitter and receiver (e.g., transceiver 2104) to excite and receive an NMR response in a geological formation. Thus, in some embodiments, a system 2100 comprises a magnet assembly to produce a magnetic field in a volume in a subterranean region, the magnet assembly comprising any or all of the components shown in FIGS. 200A, 200B, 300B, FIGS. 12-13, FIGS. 15-16, FIG. 18, and/or FIG. 20. This includes a central magnet 510 having a first axial end and a second, opposite axial end; a first end piece magnet 520 having a proximal end and a distal end, the proximal end spaced apart from the first axial end of the central magnet 510; and a second end piece magnet 530 spaced apart from the second axial end of the central magnet 510. In some embodiments, the system 2100 further comprises at least one first shim magnet 1220, 1660 disposed adjacent to or at least partially surrounded by first magnetically permeable material 1210, 1550, the at least one first shim magnet 1220, 1660 disposed next to an end of the first end piece magnet 520 that is proximal to the central magnet 510 (e.g., as is the case for magnet 1220), or next to an end of the first end piece magnet 520 that is distal to the central magnet 510 (e.g., as is the case for magnet 1660). The system 2100 further comprises a downhole tool 102 attached to the magnet assembly, further comprising a transmitter and a receiver (e.g., as the transceiver 2104) to excite and receive an NMR response in the magnetic field volume.

The tool may comprise a wireline or drilling tool. Thus, in some embodiments, of the system 2100, the downhole tool 102 comprises one of a wireline tool or a drilling tool (e.g., see FIGS. 1A, 1B, 1C).

Magnetic shims may be added to any of the configurations, and sized to provide similar or different DOIs. Thus, in some embodiments, a system 2100 comprises at least one second shim magnet 1660" adjacent to or at least partially surrounded by second magnetically permeable material 1550, the at least one second shim magnet 1660" disposed next to an end of the second end piece magnet 530 that is proximal to the central magnet 510, or next to an end of the second end piece magnet 530 that is distal to the central magnet 510, wherein geological formation depths of inspection associated with the first shim magnet 1660' and the second shim magnet 1660" are different.

One or more antennas may be added to the basic configuration. Thus, in some embodiments, a system 2100 further comprises multiple antennas 35, 36, 37A, 37B disposed at respective locations along a longitudinal axis of the tool 560, each one of the antennas 35, 36, 37A, 37B to detect a nuclear magnetic response from a respective one of multiple corresponding distinct magnetic field sub-volumes defined by the central and first and second end piece magnets 510, 520, 530. Still further embodiments may be realized.

Additional Methods

In some embodiments, a non-transitory machine-readable storage device comprises instructions stored thereon, which, when executed by a machine, transforms the machine into a customized, particular machine that performs operations comprising one or more features similar to or identical to those described with respect to the methods and techniques described herein. A machine-readable storage device, as described herein, is a physical device that stores information (e.g., instructions, data), which when stored, alters the physical structure of the device. Examples of machine-readable storage devices can include, but are not limited to, memory 2106 in the form of read only memory (ROM), random access memory (RAM), a magnetic disk storage device, an optical storage device, a flash memory, and other electronic, magnetic, or optical memory devices, including combinations thereof.

The physical structure of stored instructions may be operated on by one or more processors such as, for example, the processing unit 2102. Operating on these physical structures can cause the machine to become a specialized machine that performs operations according to methods described herein. The instructions can include instructions to cause the processing unit 2102 to store associated data or other data in the memory 2106. The memory 2106 can store the results of NMR measurements of formation parameters, drilling operation parameters, gain parameters, calibration constants, identification data, sensor location information, etc. The memory 2106 can store a log of the measurement and location information provided by the system 2100. The memory 2106 therefore may include a database, for example a relational database.

The apparatus 2110 and system 2100, and each of their elements may all be characterized as "modules" herein. Such modules may include hardware circuitry, and/or a processor and/or memory circuits, software program modules and objects, and/or firmware, and combinations thereof, as desired by the architect of the apparatus 2110 and system 2100, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, a formation imaging package, an energy detection and measurement package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 2110 and system 2100 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, vehicles, geothermal tools, NMR imaging systems, and smart transducer interface node telemetry systems, among others. Some embodiments include a number of methods.

Figure 22:
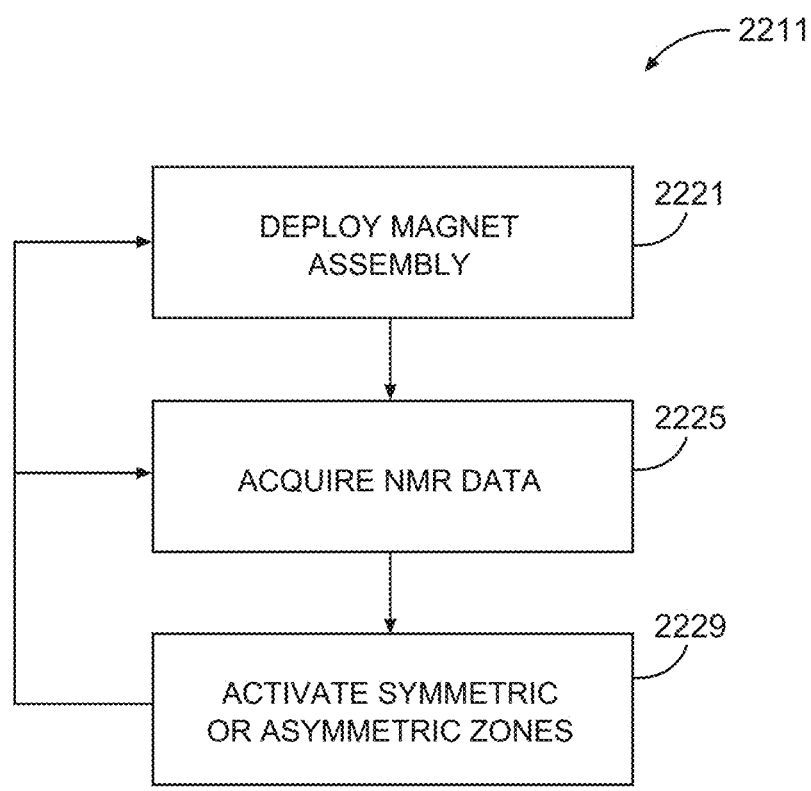
FIG. 22 is a flow chart illustrating several methods according to various embodiments.

For example, FIG. 22 is a flow chart illustrating several methods 2211 according to various embodiments. The methods 2211 may comprise processor-implemented methods, to execute on one or more processors that perform the methods. For example, one embodiment of the methods 2211 may begin at block 2221 with deploying a magnet assembly, as part of an apparatus, downhole. The apparatus may comprise any form of the apparatus 2110 illustrated in FIG. 21, for example, such as a wireline tool, or a drilling tool, etc. The method 2211 may continue on to block 2225 with the acquisition of NMR data, using the apparatus deployed in 2221. In some embodiments, the method 2211 comprises the activation of symmetric zones of sensitivity at block 2229. In some embodiments, the method 2211 comprises the activation of asymmetric zones of sensitivity at block 2229. Whether the zones are symmetric or asymmetric is determined by the configuration of the magnet assembly on the apparatus deployed in block 2221. The method 2211 may continue on to repeat the actions at blocks 2221, 2225, and/or 2229.

It should be noted that the methods described herein do not have to be executed in the order described, or in any particular order. Moreover, various activities described with respect to the methods identified herein can be executed in iterative, serial, or parallel fashion. The various elements of each method (e.g., the methods shown in FIGS. 4A, 4B, and 22) can be substituted, one for another, within and between methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein.

For example, the programs may be structured in an object-orientated format using an object-oriented language such as Java or C#. In another example, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment.

In summary, the apparatus, systems, and methods disclosed herein make use of additional shim magnets and magnetically permeable material to shape the NMR magnetic field to provide a variable DOI, with improved SNR. The resulting flexibility in tool designed may significantly enhance the value of services provided by an operation/exploration company.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

The Abstract of the Disclosure is provided to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

The invention claimed is:

1. An apparatus, comprising:
a magnet assembly to produce a magnetic field in a volume in a geological formation, the magnet assembly comprising:
a central magnet having a first axial end and a second axial end that is opposite the first axial end;
a first end piece magnet spaced apart from the first axial end of the central magnet; and
a second end piece magnet spaced apart from the second axial end of the central magnet;
multiple antennas disposed at respective locations along a longitudinal axis of a downhole tool to which the magnetic assembly is attached, each one of the antennas to detect a nuclear magnetic response from a respective one of multiple corresponding distinct magnetic field sub-volumes defined by the central and first and second end piece magnets; and
at least one first shim magnet disposed between the central magnet and the first end piece magnet, the first shim magnet disposed adjacent to or at least partially surrounded by a first magnetically permeable material, the first shim magnet to shape a first static magnetic field sub-volume provided by the central magnet and the first end piece magnet.

2. The apparatus of claim 1, further comprising:
copper radially disposed between the first shim magnet and the first magnetically permeable material, or between the central magnet and a central magnetically permeable material.

3. The apparatus of claim 1, wherein the at least one first shim magnet comprises multiple unitary ring-shaped elements and/or a series of rectangular elements shaped to form a ring.

4. The apparatus of claim 1, further comprising:
at least one second shim magnet disposed between the central magnet and the second end piece magnet, the second shim magnet disposed adjacent second magnetically permeable material or at least partially surrounded by the second magnetically permeable material and a copper material.

5. The apparatus of claim 4, further comprising:
at least one set of additional shim magnets adjacent to or at least partially surrounded by additional magnetically permeable material, to outwardly extend an arrangement of the at least one first and second shim magnets, and the first and second magnetically permeable material in a symmetrical fashion along a longitudinal axis of the tool.

6. The apparatus of claim 4, wherein geological formation depths of inspection associated with the first shim magnet and the second shim magnet are different.

7. The apparatus of claim 1, wherein the central magnet defines a first magnetic field orientation, and the first and second end piece magnets each define a second magnetic field orientation that is substantially orthogonal to the first magnetic field orientation.

8. The apparatus of claim 1, wherein at least one of the central magnet or the first and second end piece magnets comprise one or more permanent magnets.

9. The apparatus of claim 1, wherein the central magnet and the first and second end piece magnets define an overall static magnetic field volume that comprises multiple distinct sub-volumes, the multiple distinct sub-volumes including the first static magnetic field sub-volume that is elongate in a first direction parallel to a longitudinal axis of the tool the magnetic field in the first static magnetic field sub-volume being substantially uniformly oriented in the first direction, and wherein each of the antennas detect a nuclear magnetic resonance response from a respective one of the distinct sub-volumes when the antennas are operating.

10. The apparatus of claim 1, wherein conductivity of the first magnetically permeable material is selected to reduce losses in the first magnetically permeable material to less than expected losses in the antennas or the geological formation.

11. The apparatus of claim 1, further comprising:
an antenna assembly comprising a transversal-dipole antenna disposed over the central magnet, with copper and central magnetically permeable material disposed between the central magnet and the antenna assembly.

12. An apparatus, comprising:
a magnet assembly to produce a magnetic field in a volume in a subterranean region, the magnet assembly comprising:
  a central magnet having a first axial end and a second axial end that is opposite the first axial end;
  a first end piece magnet having a proximal end and a distal end, the proximal end spaced apart from the first axial end of the central magnet; and
  a second end piece magnet spaced apart from the second axial end of the central magnet;
multiple antennas disposed at respective locations along a longitudinal axis of a downhole tool to which the magnet assembly is attached, each one of the antennas to detect a nuclear magnetic response from a respective one of multiple corresponding distinct magnetic field sub-volumes defined by the central and first and second end piece magnets; and
at least one first shim magnet spaced apart from the distal end of the first end piece magnet; and
the downhole tool further comprising first magnetically permeable material disposed adjacent to or at least partially surrounding the longitudinal axis of the tool, the first magnetically permeable material disposed between the first end piece magnet and the first shim magnet.

13. The apparatus of claim 12, further comprising:
at least one second shim magnet disposed adjacent to or at least partially surrounded by the first magnetically permeable material.

14. The apparatus of claim 13, further comprising:
copper disposed between the first magnetically permeable material and the at least one second shim magnet.

15. The apparatus of claim 12, further comprising:
at least one second shim magnet spaced apart from a distal end of the second end piece magnet and second magnetically permeable material disposed between the second end piece magnet and the second shim magnet, to mirror an arrangement of the first shim magnet and the first magnetically permeable material about a center point of the central magnet.

16. The apparatus of claim 12, further comprising:
at least one second shim magnet disposed between the central magnet and the second end piece magnet and second magnetically permeable material disposed adjacent to or at least partially surrounding the at least one second shim magnet.

17. A system, comprising:
a magnet assembly to produce a magnetic field in a volume in a subterranean region, the magnet assembly comprising:
  a central magnet having a first axial end and a second axial end that is opposite the first axial end;
  a first end piece magnet having a proximal end and a distal end, the proximal end spaced apart from the first axial end of the central magnet;
  a second end piece magnet spaced apart from the second axial end of the central magnet;
  at least one first shim magnet disposed adjacent to or at least partially surrounded by first magnetically permeable material the at least one first shim magnet disposed next to an end of the first end piece magnet that is proximal to the central magnet or next to an end of the first end piece magnet that is distal to the central magnet;
a downhole tool attached to the magnet assembly, further comprising a transmitter and a receiver to excite and receive a nuclear magnetic resonance response in the magnetic field volume; and
multiple antennas disposed at respective locations along a longitudinal axis of the tool, each one of the antennas to detect a nuclear magnetic response from a respective one of multiple corresponding distinct magnetic field sub-volumes defined by the central and first and second end piece magnets.

18. The system of claim 17, wherein the downhole tool comprises one of a wireline tool or a drilling tool.

19. The system of any one of claim 17, further comprising:
at least one second shim magnet adjacent to or at least partially surrounded by second magnetically permeable material, the at least one second shim magnet disposed next to an end of the second end piece magnet that is proximal to the central magnet, or next to an end of the second end piece magnet that is distal to the central magnet, wherein geological formation depths of inspection associated with the first shim magnet and the second shim magnet are different.

* * * * *